US011896701B2

United States Patent
Jaiser et al.

(10) Patent No.: US 11,896,701 B2
(45) Date of Patent: Feb. 13, 2024

(54) METHOD FOR DYEING KERATIN MATERIAL, COMPRISING THE USE OF AN ORGANIC C1-C6 ALKOXY SILANE AND TANNIC ACID

(71) Applicant: Henkel AG & Co. KGaA, Duesseldorf (DE)

(72) Inventors: Phillip Jaiser, Langenfeld (DE); Marc Nowottny, Moenchengladbach (DE); Carsten Mathiaszyk, Essen (DE); Gabriele Weser, Neuss (DE); Torsten Lechner, Langenfeld (DE); Caroline Kriener, Duesseldorf (DE); Juergen Schoepgens, Schwalmtal (DE); Ulrike Schumacher, Duesseldorf (DE); Claudia Kolonko, Remscheid (DE); Udo Erkens, Willich (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/785,874

(22) PCT Filed: Oct. 16, 2020

(86) PCT No.: PCT/EP2020/079170
§ 371 (c)(1),
(2) Date: Jun. 15, 2022

(87) PCT Pub. No.: WO2021/121718
PCT Pub. Date: Jun. 24, 2021

(65) Prior Publication Data
US 2023/0063028 A1 Mar. 2, 2023

(30) Foreign Application Priority Data
Dec. 16, 2019 (DE) .......................... 102019219715.9

(51) Int. Cl.
*A61Q 5/10* (2006.01)
*A61K 8/58* (2006.01)
*A61K 8/49* (2006.01)

(52) U.S. Cl.
CPC .............. *A61K 8/585* (2013.01); *A61K 8/498* (2013.01); *A61Q 5/10* (2013.01); *A61K 2800/4324* (2013.01); *A61K 2800/884* (2013.01)

(58) Field of Classification Search
CPC .................... A61K 8/585; A61K 8/498; A61K 2800/4324; A61K 2800/884; A61K 8/19; A61K 8/602; A61K 2800/43; A61K 2800/4322; A61Q 5/10; A61Q 5/065
USPC ............................................................ 8/405
See application file for complete search history.

(56) References Cited

U.S. PATENT DOCUMENTS

| | | | | |
|---|---|---|---|---|
| 2001/0007160 | A1* | 7/2001 | Yamaguchi ............... | A61Q 5/10 8/405 |
| 2010/0083446 | A1* | 4/2010 | Brun ...................... | A61K 8/891 8/405 |
| 2010/0303748 | A1* | 12/2010 | Hercouet ................. | A61Q 5/10 8/405 |

FOREIGN PATENT DOCUMENTS

| | | |
|---|---|---|
| EP | 2168633 A2 | 3/2010 |
| FR | 2880801 A1 | 7/2006 |
| FR | 2966356 A1 | 4/2012 |
| WO | 2013068979 A2 | 5/2013 |

\* cited by examiner

*Primary Examiner* — Eisa B Elhilo
(74) *Attorney, Agent, or Firm* — Lorenz & Kopf, LLP

(57) ABSTRACT

The subject of the present disclosure is a process for dyeing keratinous material, in particular human hair. The process includes applying a first composition (A) to the keratinous material. The first composition includes (A1) one or more organic $C_1$-$C_6$ alkoxysilanes and/or condensation products thereof, and (A2) at least one colorant compound selected from the group of pigments and direct dyes. A second composition (B) is applied to the keratinous material. The second composition (B) includes (B1) Tannic acid.

14 Claims, No Drawings

METHOD FOR DYEING KERATIN MATERIAL, COMPRISING THE USE OF AN ORGANIC C1-C6 ALKOXY SILANE AND TANNIC ACID

CROSS-REFERENCE TO RELATED APPLICATION

This application is a U.S. National-Stage entry under 35 U.S.C. § 371 based on International Application No. PCT/EP2020/079170, filed Oct. 16, 2020, which was published under PCT Article 21(2) and which claims priority to German Application No. 102019219715.9, filed Dec. 16, 2019, which are all hereby incorporated in their entirety by reference.

TECHNICAL FIELD

The present application is in the field of cosmetics and concerns a process for coloring keratinous material, in particular human hair, which comprises the use of two compositions (A) and (B). Composition (A) is a composition comprising at least one $C_1$-$C_6$ organic alkoxysilane (A1) and at least one coloring compound (A2). The application further describes multi-component packaging units (kit-of-parts) for dyeing keratinous material.

Changing the shape and color of keratinous fibers, especially hair, is an important area of modern cosmetics. To change the color of the hair, the specialist knows various coloring systems, depending on the requirements of coloring. For permanent, intensive dyeings with good fixing properties and good gray coverage, oxidation dyes are usually used. Such colorants usually contain oxidation dye precursors, so-called developer components and coupler components, which form the actual dyes under the influence of oxidizing agents such as hydrogen peroxide among themselves. Oxidation dyes are exemplified by very long-lasting dyeing results.

BACKGROUND

When using direct dyes, already formed dyes are transmitted from the colorant into the hair fiber. Compared to oxidative hair dyeing, the dyeings obtained with direct dyes have lower durability and faster washout. Dyeing with direct dyes usually remains on the hair for a period of between 5 and 20 washes.

For short-term color changes on the hair and/or skin, the use of color pigments is known. Color pigments are generally understood to be insoluble, color-imparting substances. These are present undissolved in the form of small particles in the coloring formulation and are merely deposited externally on the hair fibers and/or skin surface. Therefore, they can usually be removed without residue by a few washes with surfactant-comprising cleaning agents. Various products of this type are available on the market under the name of hair mascara.

EP 2168633 B1 deals with the task of producing long-lasting hair colorations using pigments. The paper illustrates that when a combination of pigment, organic silicon compound, hydrophobic polymer and a solvent is used on hair, it is possible to produce colorations that are particularly resistant to friction and/or shampooing.

The organic silicon compounds used in EP 2168633 B1 are reactive compounds from the alkoxysilane class. These alkoxysilanes hydrolyze at high rates in the presence of water and form hydrolysis products and/or condensation products, depending on the amounts of alkoxysilane and water used in each case.

When these alkoxysilanes or their hydrolysis or condensation products are applied to keratinous material, a film or coating is formed on the keratinous material, which completely envelops the keratinous material and in this way strongly influences the properties of the keratinous material. Possible areas of application include permanent styling or permanent shape modification of keratin fibers. In this process, the keratin fibers are automatically shaped into the desired form and then fixed in this form by forming the coating described above. Another particularly suitable application is the coloring of keratin material; in this application, the coating or film is produced in the presence of a coloring compound, for example a pigment. The film colored by the pigment remains on the keratin material or keratin fibers and results in surprisingly wash-resistant colorations.

A major advantage of the alkoxysilane-based dyeing principle is that the high reactivity of this class of compounds enables very fast treatment. This means that good staining results can be achieved even after short application periods of just a few minutes. The shorter the exposure times of the hair treatment products, the greater the comfort for the user. With regard to the durability of the dyeing, in particular its washing and/or friction resistance, there is still room for improvement.

BRIEF SUMMARY

In an exemplary embodiment, a method of dyeing keratinous material, in particular human hair, includes applying a first composition (A) to the keratinous material. The first composition (A) includes (A1) one or more organic C1-C6 alkoxysilanes and/or condensation products thereof, and (A2) at least one colorant compound selected from the group of pigments, direct dyes, or combinations thereof. A second composition (B) is applied to the keratinous material. The second composition (B) includes (B1) Tannic acid.

In another exemplary embodiment, a multi-component packaging unit (kit-of-parts) for dyeing keratinous material, includes, separately prepared, a first container having a first composition (A) including (A1) one or more C1-C6 organic alkoxysilanes and/or condensation products thereof, and (A2) at least one colorant compound selected from the group of pigments and direct dyes. A second container having a second composition (B) includes (B1) tannic acid.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was the task of the present application to find a process for dyeing keratinous material which shows improvements in terms of color intensity and fixing properties. In particular, the color intensity, the wash resistance and also the friction resistance should be improved compared to the colorations that can be achieved so far with the formulations known from the prior art.

Surprisingly, it has been found that this task can be fully solved if the keratin material is dyed in a process in which two compositions (A) and (B) are applied to the keratin material. Here, the first composition (A) comprises at least one organic $C_1$-$C_6$ alkoxysilane and/or their condensation product and furthermore at least one color-imparting compound. The second composition (B) is exemplified by a content of tannic acid.

A first object of the present disclosure is a method for coloring keratinous material, in particular human hair, wherein on the keratinous material are applied:
- a first composition (A) comprising:
  - (A1) one or more organic $C_1$-$C_6$ alkoxysilanes and/or condensation products thereof, and
  - (A2) at least one colorant compound selected from the group of pigments and direct dyes
- a second composition (B) comprising:
  - (B1) Tannic acid.

If the composition (A) was applied to the keratin material as part of a dyeing process, an increase in color intensity was observed in particular if the composition (B) was applied to the keratin material in the form of an aftertreatment agent after application of the composition (A). In addition to the enhancement of color intensity, an improvement in wash fastness and rub fastness was surprisingly also observed in this context.

Treatment of Keratinous Material

Keratinous material or keratinous material means hair, the skin, the nails (such as fingernails and/or toenails). Furthermore, wool, fur and feathers also fall under the definition of keratinous material.

Preferably, keratinous material is understood to mean human hair, human skin and human nails, in particular fingernails and toenails. More specifically, keratinous material is understood to mean human hair.

The term "composition for coloring" is used in the context of the present disclosure for a coloring of the keratin material, in particular of the hair, caused by the use of coloring compounds, such as thermochromic and photochromic dyes, pigments, mica, direct dyes. During this coloring process, the aforementioned coloring compounds are deposited in a particularly homogeneous and smooth film on the surface of the keratin material or are transmitted to the keratin fiber. The film forms in situ by oligomerization or polymerization of the organic alkoxysilane(s), and by the interaction of the color-imparting compound and organic silicon compound and optionally other ingredients, such as a film-forming, polymer.

Organic $C_1$-$C_6$ Alkoxysilanes (A1) and/or their Condensation Products in the Composition (A)

The composition (A) is wherein it comprises one or more organic $C_1$-$C_6$ alkoxysilanes (A1) and/or their condensation products.

The organic $C_1$-$C_6$ alkoxysilane(s) are organic, non-polymeric silicon compounds, preferably selected from the group of silanes having one, two or three silicon atoms Organic silicon compounds, alternatively referred to as organosilicon compounds, are compounds that either have a direct silicon-carbon (Si—C) bond or in which the carbon is attached to the silicon atom via an oxygen, nitrogen or sulfur atom. The organic silicon compounds of the present disclosure are preferably compounds comprising one to three silicon atoms. Particularly preferably, the organic silicon compounds contain one or two silicon atoms.

According to the IUPAC rules, the term silane stands for a group of substances of chemical compounds based on a structure of silicon and hydrogen. In organic silanes, the hydrogen atoms are wholly or partially replaced by organic groups such as (substituted) alkyl groups and/or alkoxy groups.

A characteristic feature of the $C_1$-$C_6$ alkoxysilanes is that at least one $C_1$-$C_6$ alkoxy group is directly bonded to a silicon atom. The $C_1$-$C_6$ alkoxysilanes as contemplated herein thus comprise at least one structural unit R'R"R'''Si—O—($C_1$-$C_6$ alkyl) where the radicals R', R" and R''' represent the three remaining bond valencies of the silicon atom.

The $C_1$-$C_6$ alkoxy group or groups bonded to the silicon atom are very reactive and are hydrolyzed at high rates in the presence of water, the reaction rate depending, among other things, on the number of hydrolyzable groups per molecule. If the hydrolysable $C_1$-$C_6$ alkoxy group is an ethoxy group, the organic silicon compound preferably comprises a structural unit R'R"R'''Si—O—CH2-CH3. The R', R" and R'''radicals again represent the three remaining free valencies of the silicon atom.

Even the addition of small amounts of water leads first to hydrolysis and then to a condensation reaction between the organic alkoxysilanes. For this reason, both the organic alkoxysilanes (A1) and their condensation products may be present in the composition.

A condensation product is understood to be a product formed by the reaction of at least two organic $C_1$-$C_6$ alkoxysilanes with elimination of water and/or with elimination of a $C_1$-$C_6$ alkanol.

The condensation products can be, for example, dimers, but also trimers or oligomers, with the condensation products being in equilibrium with the monomers.

Depending on the amount of water used or consumed in the hydrolysis, the equilibrium shifts from monomeric $C_1$-$C_6$ alkoxysilane to condensation product.

In a very particularly preferred embodiment, a process is wherein the composition (A) comprises one or more organic $C_1$-$C_6$ alkoxysilanes (A1) selected from silanes having one, two or three silicon atoms, the organic silicon compound further comprising one or more basic chemical functions.

This basic group can be, for example, an amino group, an alkylamino group or a dialkylamino group, which is preferably connected to a silicon atom via a linker. Preferably, the basic group is an amino group, a $C_1$-$C_6$ alkylamino group or a di($C_1$-$C_6$)alkylamino group.

A very particularly preferred method is wherein the composition (A) comprises one or more organic $C_1$-$C_6$ alkoxysilanes (A1) selected from the group of silanes having one, two or three silicon atoms, and wherein the $C_1$-$C_6$ alkoxysilanes further comprise one or more basic chemical functions.

Particularly good results were obtained when $C_1$-$C_6$ alkoxysilanes of the formula (S-I) and/or (S-II) were used in the process. Since, as previously described, hydrolysis/condensation already starts at traces of moisture, the condensation products of the $C_1$-$C_6$ alkoxysilanes of formula (S-I) and/or (S-II) are also included in this embodiment.

In another very particularly preferred embodiment, a process is wherein the first composition (A) comprises one or more organic $C_1$-$C_6$ alkoxysilanes (A1) of the formula (S-I) and/or (S-II), $$R_1R_2N\text{-}L\text{-}Si(OR_3)_a(R_4)_b \tag{S-I}$$

where
- $R_1$, $R_2$ independently represent a hydrogen atom or a $C_1$-$C_6$ alkyl group,
- L is a linear or branched, divalent $C_1$-$C_{20}$ alkylene group,
- $R_3$, $R_4$ are independent of each other for a $C_1$-$C_6$ alkyl group,
- a, represents an integer from 1 to 3, and
- b is the integer 3-a, and

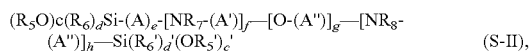

(S-II), where
R5, R5', R5", R6, R6' and R6" independently represent a C1-C6 alkyl group,
A, A', A", A''' and A'''' independently represent a linear or branched $C_1$-$C_{20}$ divalent alkylene group,
$R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (S-III),

(S-III), c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
with the proviso that at least one of the radicals from e, f, g and h is different from 0, and/or their condensation products.

The substituents $R_1$, $R_2$, $R_3$, $R_4$, $R_5$, $R_5'$, $R_5"$, $R_6$, $R_6'$, $R_6"$, $R_7$, $R_8$, L, A, A', A", A''' and A'''' in the compounds of formula (S-I) and (S-II) are exemplified below:
Examples of a $C_1$-$C_6$ alkyl group include methyl, ethyl, propyl, isopropyl, n-butyl, s-butyl and t-butyl, n-pentyl and n-hexyl groups. Propyl, ethyl and methyl are preferred alkyl radicals. Examples of a $C_2$-$C_6$ alkenyl group are vinyl, allyl, but-2-enyl, but-3-enyl as well as isobutenyl, preferred $C_2$-$C_6$ alkenyl radicals are vinyl and allyl. Preferred examples of a hydroxy-C1-C6-alkyl group include a hydroxymethyl, a 2-hydroxyethyl, a 2-hydroxypropyl, a 3-hydroxypropyl, a 4-hydroxybutyl, a 5-hydroxypentyl and a 6-hydroxyhexyl group; a 2-hydroxyethyl group is particularly preferred. Examples of an amino-$C_1$-$C_6$-alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—$CH_2$—), the ethylene group (—$CH_2$—$CH_2$—), the propylene group (—$CH_2$—$CH_2$— $CH_2$—), and the butylene group (—$CH_2$—$CH_2$—$CH_2$— $CH_2$—). The propylene group (—CH2-CH2-CH2-) is particularly preferred. From a chain length of 3 C atoms, divalent alkylene groups can also be branched. Examples of branched C3-C20 divalentalkylene groups are (—$CH_2$—CH ($CH_3$)—) and (—$CH_2$—CH($CH_3$)—$CH_2$—).

In the organic silicon compounds of the formula (S-I)

(S-I), $R_1$ and $R_2$ independently represent a hydrogen atom or a $C_1$-$C_6$ alkyl group. Very preferably, $R_1$ and $R_2$ both represent a hydrogen atom.

In the middle part of the organic silicon compound is the structural unit or linker -L- which stands for a linear or branched, divalent $C_1$-$C_{20}$ alkylene group. The divalent $C_1$-$C_{20}$ alkylene group may alternatively be referred to as a divalent or divalent $C_1$-$C_{20}$ alkylene group, by which is meant that each -L- grouping may form two bonds.

Preferably, -L- represents a linear, divalent $C_1$-$C_{20}$ alkylene group. Further preferably, -L- represents a linear divalent $C_1$-$C_6$ alkylene group. Particularly preferably, -L- stands for a methylene group (—$CH_2$—), an ethylene group (—$CH_2$—$CH_2$—), a propylene group (—$CH_2$—$CH_2$— $CH_2$—) or a butylene group (—$CH_2$—$CH_2$—$CH_2$— $CH_2$—). Very preferably, L represents a propylene group (—$CH_2$—$CH_2$—$CH_2$—).

The organic silicon compounds of the formula (S-I) as contemplated herein

(S-I), carry the silicon-comprising grouping —$Si(OR_3)_a(R_4)_b$ at one end.

In the terminal structural unit —$Si(OR_3)_a(R_4)_b$, $R_3$ and $R_4$ independently represent a $C_1$-$C_6$ alkyl group, Particularly preferably, $R_3$ and $R_4$ independently represent a methyl group or an ethyl group.

Here, a represents an integer from 1 to 3, and b represents the integer 3-a. If a represents the number 3, then b is 0. If a stands for the number 2, then b is equal to 1. If a stands for the number 1, then b is equal to 2.

Keratin treatment agents with particularly good properties could be prepared if composition (A) comprises at least one organic $C_1$-$C_6$ alkoxysilane of the formula (S-I) in which the radicals $R_3$, $R_4$ independently of one another represent a methyl group or an ethyl group.

Furthermore, dyeings with the best wash fastnesses could be obtained if the composition (A) comprises at least one organic $C_1$-$C_6$-alkoxysilane of the formula (S-I) in which the radical a represents the number 3. In this case, the remainder b stands for the number 0.

In another preferred embodiment, a process is wherein the composition (A) comprises one or more organic $C_1$-$C_6$ alkoxysilanes of formula (S-I),
where
$R_3$, $R_4$ independently represent a methyl group or an ethyl group, and
a stands for the number 3 and
b stands for the number 0.

In another preferred embodiment, a process is wherein the composition (A) comprises at least one or more organic $C_1$-$C_6$ alkoxysilanes of formula (S-I),

(S-I), where
$R_1$, $R_2$ both represent a hydrogen atom, and
L is a linear, divalent $C_1$-$C_6$ alkylene group, preferably a propylene group (—$CH_2$—$CH_2$—$CH_2$—) or an ethylene group (—$CH_2$—$CH_2$—),
$R_3$ represents an ethyl group or a methyl group,
$R_4$ represents a methyl group or an ethyl group,
a stands for the number 3 and
b stands for the number 0.

Organic silicon compounds of the formula (I) which are particularly suitable for solving the problem are

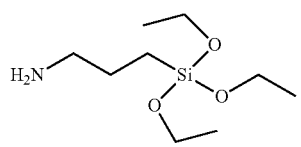 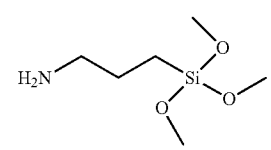

(3-Aminopropyl)triethoxysilane    (3-Aminopropyl)trimethoxysilane

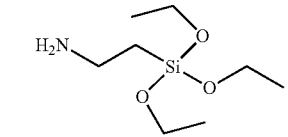 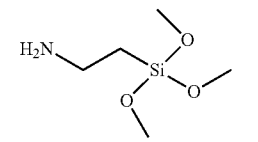

(2-Aminoethyl)triethoxysilane    (2-Aminoethyl)trimethoxysilane

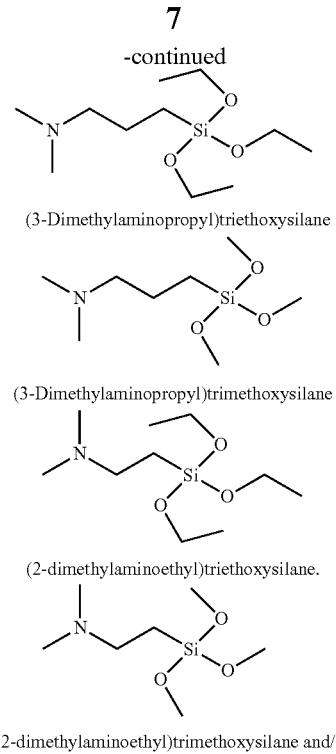

(3-Dimethylaminopropyl)triethoxysilane (3-Dimethylaminopropyl)trimethoxysilane (2-dimethylaminoethyl)triethoxysilane.

(2-dimethylaminoethyl)trimethoxysilane and/or

In another preferred embodiment, a process is wherein the first composition (A) comprises at least one $C_1$-$C_6$ organic alkoxysilane (A1) of formula (S-I) selected from the group of
(3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-dimethylaminoethyl)triethoxysilane,
(2-Dimethylaminoethyl)trimethoxysilane
and/or their condensation products.

The aforementioned organic silicon compounds of formula (I) are commercially available.

(3-Aminopropyl)trimethoxysilane is available for purchase from Sigma-Aldrich, for example.

(3-Aminopropyl)triethoxysilane is also commercially available from Sigma-Aldrich.

In another embodiment of the method, the composition (A) may also comprise one or more organic $C_1$-$C_6$ alkoxysilanes of formula (S-II),

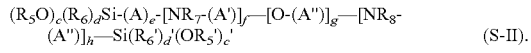
(S-II).

The organosilicon compounds of the formula (S-II) each bear at their two ends the silicon-comprising groupings $(R_5O)_c(R_6)_dSi$— and —$Si(R_6')_{d'}(OR_5')_{c'}$.

In the middle part of the molecule of formula (S-II) there are the groupings -(A)$_e$- and —[NR$_7$-(A')]$_f$- and —[O-(A'')]$_g$- and —[NR-(A'')]$_h$-. Here, each of the radicals e, f, g and h can independently represent the number 0 or 1, with the proviso that at least one of the radicals e, f, g and h is other than 0. In other words, an organic silicon compound of formula (II) as contemplated herein comprises at least one grouping selected from the group of -(A)- and —[NR$_7$-(A')]- and —[O-(A'')]- and —[NR$_8$-(A''')]-.

In the two terminal structural units $(R_5O)_c(R_6)_dSi$— and —$Si(R_6')_{d'}(OR_5')_{c'}$, the radicals R5, R5', R5'' independently represent a $C_1$-$C_6$ alkyl group. The R6, R6' and R6'' radicals independently represent a $C_1$-$C_6$ alkyl group.

Here, c represents an integer from 1 to 3, and d represents the integer 3-c. If c stands for the number 3, then d is 0. If c stands for the number 2, then d is equal to 1. If c stands for the number 1, then d is equal to 2.

Similarly, c' represents an integer from 1 to 3, and d' represents the integer 3-c'. If c' stands for the number 3, then d' is equal to 0. If c' stands for the number 2, then d' is equal to 1. If c' stands for the number 1, then d' is equal to 2.

Stains with the best wash fastnesses could be obtained when the radicals c and c' both stand for the number 3. In this case, d and d' both stand for the number 0.

In another preferred embodiment, a process is wherein the composition (A) comprises one or more organic $C_1$-$C_6$ alkoxysilanes of formula (S-II),

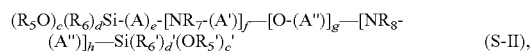
(S-II), where
R5 and R5' independently represent a methyl group or an ethyl group,
c and c' both stand for the number 3 and
d and d' both stand for the number 0.

When c and c' are both 3 and d and d' are both 0, the organic silicon compounds as contemplated herein correspond to the formula (S-IIa)

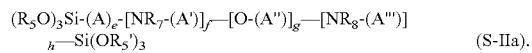
(S-IIa).

The radicals e, f, g, and h can independently represent the number 0 or 1, with at least one residue from e, f, g, and h being different from zero. The abbreviations e, f, g and h thus define which of the groupings -(A)$_e$- and —[NR$_7$-(A')]$_f$- and —[O-(A'')]$_g$- and —[NR$_8$-(A''')]$_h$- are located in the middle part of the organic silicon compound of formula (II).

In this context, the presence of certain groupings has proven to be particularly advantageous in terms of achieving washfast dyeing results. Particularly good results could be obtained if at least two of the radicals e, f, g and h stand for the number 1. Very preferably, e and f both stand for the number 1. Furthermore, g and h both represent the number 0.

When e and f are both 1 and g and h are both 0, the organic silicon compounds as contemplated herein are represented by the formula (S-IIb)

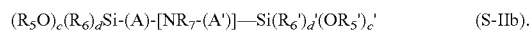
(S-IIb).

Radicals A, A', A'', A''' and A'''' independently represent a linear or branched $C_1$-$C_{20}$ divalent alkylene group. Preferably, A, A', A'', A''' and A'''' independently represent a linear divalent $C_1$-$C_{20}$ alkylene group. Further preferably, A, A', A'', A''' and A'''' independently represent a linear divalent $C_1$-$C_6$ alkylene group.

The divalent $C_1$-$C_{20}$ alkylene group may alternatively be referred to as a divalent or divalent $C_1$-$C_{20}$ alkylene group, by which is meant that each grouping A, A', A'', A''' and A''' may form two bonds.

Particularly preferably, the radicals A, A', A'', A''' and A'''' independently represent a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). Very preferably, the radicals A, A', A'', A''' and A'''represent a propylene group (—CH$_2$—CH$_2$—CH$_2$—).

When the radical f represents the number 1, the organic silicon compound of formula (II) as contemplated herein comprises a structural grouping —[NR$_7$-(A')]-.

When the radical h represents the number 1, the organic silicon compound of formula (II) as contemplated herein comprises a structural grouping —[NR$_8$-(A")]-.

Here, R$_7$ and R$_8$ independently represent a hydrogen atom, a C$_1$-C$_6$ alkyl group, a hydroxy-C$_1$-C$_6$ alkyl group, a C$_2$-C$_6$ alkenyl group, an amino-C$_1$-C$_6$ alkyl group or a group of the formula (S-III)

Very preferably, R7 and R8 independently represent a hydrogen atom, a methyl group, a 2-hydroxyethyl group, a 2-alkenyl group, a 2-aminoethyl group or a group of formula (S-III).

When the radical f represents the number 1 and the radical h represents the number 0, the organic silicon compound as contemplated herein comprises the grouping [NR$_7$-(A')] but not the grouping —[NR$_8$-(A")]. If the radical R7 now stands for a grouping of formula (III), the organic silicon compound comprises 3 reactive silane groups.

In another preferred embodiment, a method is wherein the composition (A) comprises one or more C$_1$-C$_6$ organic alkoxysilanes (A1) of formula (S-II)

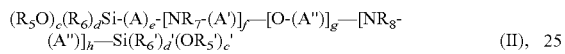

where
e and f both stand for the number 1,
g and h both stand for the number 0,
A and A' independently of one another represent a linear, divalent C$_1$-C$_6$ alkylene group and
R7 represents a hydrogen atom, a methyl group, a 2-hydroxyethyl group, a 2-alkenyl group, a 2-aminoethyl group or a group of the formula (S-III).

In another preferred embodiment, a method is wherein the composition (A) comprises one or more C$_1$-C$_6$ organic alkoxysilanes (A1) of formula (S-II), wherein
e and f both stand for the number 1,
g and h both stand for the number 0,
A and A' independently represent a methylene group (—CH$_2$—), an ethylene group (—CH$_2$—CH$_2$—) or a propylene group (—CH$_2$—CH$_2$—CH$_2$—),
and
R7 represents a hydrogen atom, a methyl group, a 2-hydroxyethyl group, a 2-alkenyl group, a 2-aminoethyl group or a group of the formula (S-III).

Organic silicon compounds of the formula (S-II) which are well suited for solving the problem as contemplated herein are

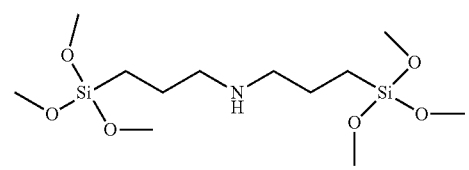

3-(Trimethoxysilyl)-N-[3-(trimethoxysilyl)propyl]-1-propanamine

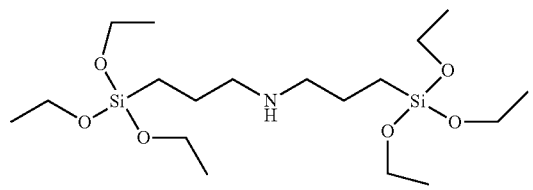

3-(Triethoxysilyl)-N-[3-(triethoxysilyl)propyl]-1-propanamine

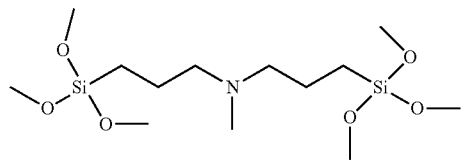

N-methyl-3-(trimethoxysilyl)-N-[3(trimethoxysilyl)propyl]-1-propanamine

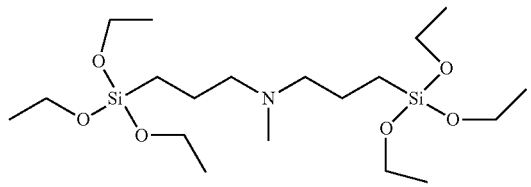

N-methyl-3-(triethoxysilyl)-N-[3-(triethoxysilyl)propyl]-1-propanamine

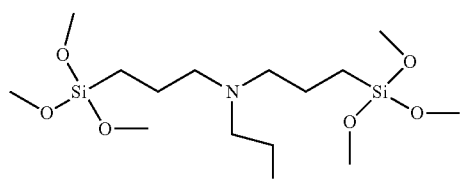

2-[Bis[3-(trimethoxysilyl)propyl]amino]ethanol

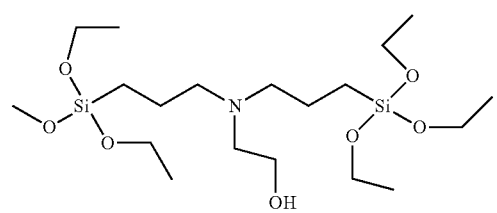

2-[Bis[3-(triethoxysilyl)propyl]amino]ethanol

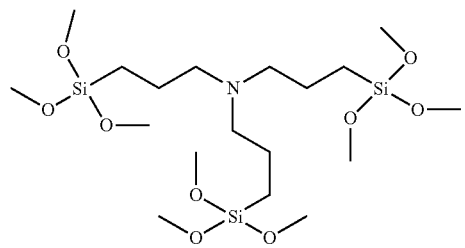

3-(Trimethoxysilyl)-N,N-bis[3-(trimethoxysilyl)propyl]-1-propanamine

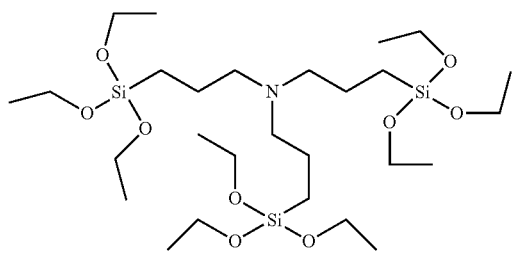

3-(Triethoxysilyl)-N,N-bis[3-(triethoxysilyl)propyl]-1-propanamine

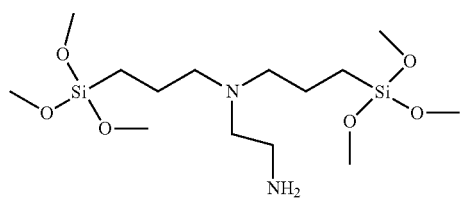

N1,N1-bis[3-trimethoxysilyl)propyl]-1,2-ethanediamine

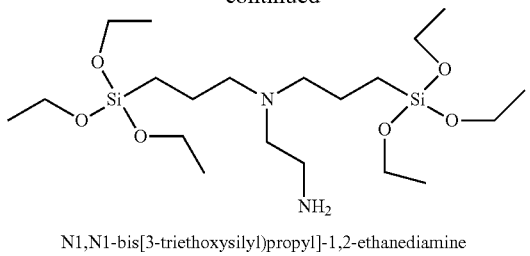

N1,N1-bis[3-triethoxysilyl)propyl]-1,2-ethanediamine

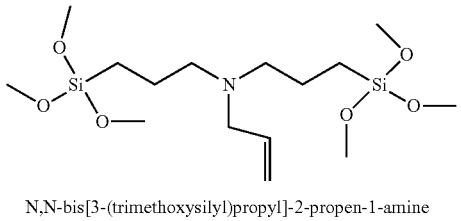

N,N-bis[3-(trimethoxysilyl)propyl]-2-propen-1-amine

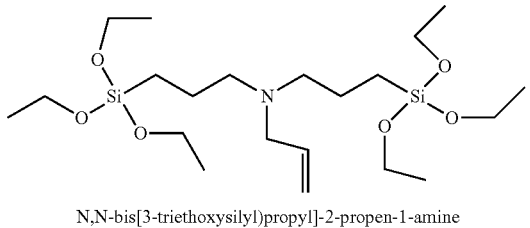

N,N-bis[3-triethoxysilyl)propyl]-2-propen-1-amine

The aforementioned organic silicon compounds of formula (S-II) are commercially available.

Bis(trimethoxysilylpropyl)amines with CAS number 82985-35-1 can be purchased from Sigma-Aldrich, for example.

Bis[3-(triethoxysilyl)propyl]amines with CAS number 13497-18-2 can be purchased from Sigma-Aldrich, for example.

N-methyl-3-(trimethoxysilyl)-N-[3-(trimethoxysilyl)propyl]-1-propanamine is alternatively known as bis(3-trimethoxysilylpropyl)-N-methylamine and can be purchased commercially from Sigma-Aldrich or Fluorochem.

3-(Triethoxysilyl)-N,N-bis[3-(triethoxysilyl)propyl]-1-propanamine with CAS number 18784-74-2 can be purchased from Fluorochem or Sigma-Aldrich, for example.

In another preferred embodiment, a process is wherein the composition (A) comprises one or more $C_1$-$C_6$ organic alkoxysilanes of formula (S-II) selected from the group of
3-(Trimethoxysilyl)-N-[3-(trimethoxysilyl)propyl]-1-propanamine
3-(Triethoxysilyl)-N-[3-(triethoxysilyl)propyl]-1-propanamine
N-methyl-3-(trimethoxysilyl)-N-[3-(trimethoxysilyl)propyl]-1-propanamine
N-methyl-3-(triethoxysilyl)-N-[3-(triethoxysilyl)propyl]-1-propanamine
2-[Bis[3-(trimethoxysilyl)propyl]amino]ethanol
2-[Bis[3-(triethoxysilyl)propyl]amino]ethanol
3-(Trimethoxysilyl)-N,N-bis[3-(trimethoxysilyl)propyl]-1-propanamine
3-(triethoxysilyl)-N,N-bis[3-(triethoxysilyl)propyl]-1-propanamine
N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propen-1-amine and/or
N,N-bis[3-(triethoxysilyl)propyl]-2-propen-1-amine,
and/or their condensation products.

In further dyeing tests, it has also been found to be particularly advantageous if at least one organic $C_1$-$C_6$ alkoxysilane (A1) of the formula (S-IV) was used in the process $R_9Si(OR_{10})_k(R_{11})_m$ (S-IV).

The compounds of formula (S-IV) are organic silicon compounds selected from silanes having one, two or three silicon atoms, wherein the organic silicon compound comprises one or more hydrolyzable groups per molecule.

The organic silicon compound(s) of formula (S-IV) may also be referred to as silanes of the alkyl-$C_1$-$C_6$ alkoxysilane type, $$R_9Si(OR_{10})_k(R_{11})_m \quad \text{(S-IV)},$$

where
$R_9$ represents a $C_1$-$C_{12}$ alkyl group,
$R_{10}$ stands for a $C_1$-$C_6$ alkyl group,
$R_{11}$ stands for a $C_1$-$C_6$ alkyl group
k is an integer from 1 to 3, and
m stands for the integer 3-k.

In a further embodiment, a particularly preferred method is to wherein the first composition (A) comprises one or more organic $C_1$-$C_6$ alkoxysilanes (A1) of the formula (S-IV), $$R_9Si(OR_{10})_k(R_{11})_m \quad \text{(S-IV)},$$

where
$R_9$ represents a $C_1$-$C_{12}$ alkyl group,
$R_{10}$ stands for a $C_1$-$C_6$ alkyl group,
$R_{11}$ stands for a $C_1$-$C_6$ alkyl group
k is an integer from 1 to 3, and
m stands for the integer 3-k,
and/or their condensation products.

In the organic $C_1$-$C_6$ alkoxysilanes of the formula (S-IV), the radical $R_9$ represents a $C_1$-$C_{12}$ alkyl group. This $C_1$-$C_{12}$ alkyl group is saturated and can be linear or branched. Preferably, $R_9$ represents a linear $C_1$-$C_8$ alkyl group. Preferably, $R_9$ represents a methyl group, an ethyl group, an n-propyl group, an n-butyl group, an n-pentyl group, an n-hexyl group, an n-octyl group, an n-dodecyl group or an n-octadecyl group. Particularly preferably, $R_9$ represents a methyl group, an ethyl group or an n-hexyl group.

In the organic silicon compounds of formula (S-IV), the $R_{10}$ radical represents a $C_1$-$C_6$ alkyl group. Particularly preferably, $R_{10}$ represents a methyl group or an ethyl group.

In the organic silicon compounds of formula (S-IV), the radical $R_{11}$ represents a $C_1$-$C_6$ alkyl group. Particularly preferably, $R_{11}$ represents a methyl group or an ethyl group.

Furthermore, k stands for an integer from 1 to 3, and m stands for the integer 3-k. If k stands for the number 3, then m is 0. If k stands for the number 2, then m is equal to 1. If k stands for the number 1, then m is equal to 2.

Dyeings with the best wash fastnesses could be obtained when the composition (A) comprises at least one organic $C_1$-$C_6$ alkoxysilane (A1) of formula (S-IV) in which the radical k represents the number 3. In this case, the remainder m stands for the number 0.

Organic silicon compounds of the formula (S-IV) that are particularly suitable for solving the problem are

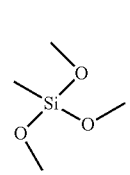 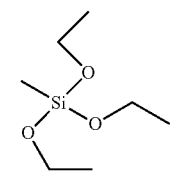

Methyltrimethoxysilane    Methyltriethoxysilane

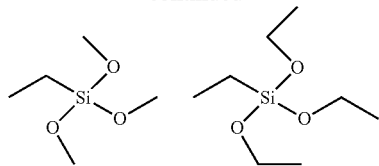

Ethyltrimethoxysilane    Ethyltriethoxysilane

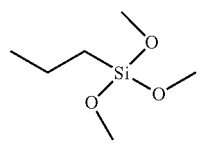

n-Propyltrimethoxysilane (also known as propyltrimethoxysilane)

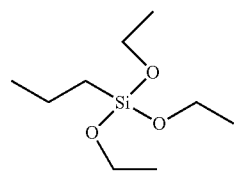

n-Propyltriethoxysilane (also known as propyltriethoxysilane)

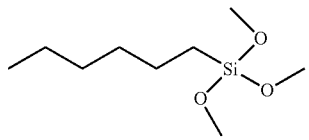

n-Hexyltrimethoxysilane (also referred to as hexyltrimethoxysilane)

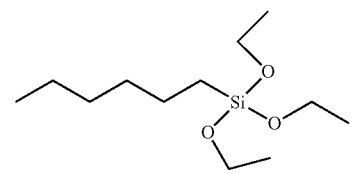

n-Hexyltriethoxysilane (also referred to as hexyltriethoxysilane)

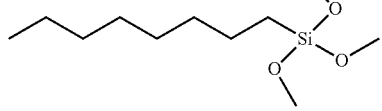

n-Octyltrimethoxysilane (also referred to as octyltrimethoxysilane)

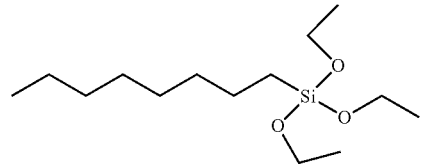

n-Octyltriethoxysilane (also referred to as octyltriethoxysilane)

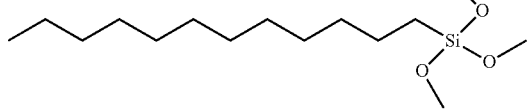

n-Dodecyltrimethoxysilane (also referred to as dodecyltrimethoxysilane) and/or

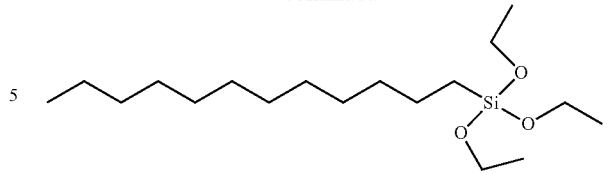

n-Dodecyltriethoxysilane (also referred to as dodecyltriethoxysilane) and n-octadecyltrimethoxysilane (also known as octadecyltrimethoxysilan and/or n-octadecyltriethoxysilane (also known as dodecyltriethoxysilane).

In another preferred embodiment, a method is wherein the first composition (A) comprises at least one $C_1$-$C_6$ organic alkoxysilane (A1) of formula (S-IV) selected from the group of
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane,
Octadecyltrimethoxysilane,
Octadecyltriethoxysilane,
their mixtures
and/or their condensation products.

In another preferred embodiment, a method is wherein the first composition (A) comprises at least two structurally different organic silicon compounds.

In a particularly preferred embodiment, a method is wherein the first composition (A) comprises at least one organic silicon compound of formula (I) and at least one organic silicon compound of formula (IV).

In a further, very preferred embodiment, a method is wherein the first composition comprises (A):
at least one first organic silicon compound selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and (2-dimethylaminoethyl)triethoxysilane, and
at least one second organic silicon compound selected from the group of methyltrimethoxysilane, methyltriethoxysilane, ethyltrimethoxysilane, ethyltriethoxysilane, propyltrimethoxysilane, Propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

In a further, very particularly preferred embodiment, a method is wherein the first composition comprises (A):
at least one first organic silicon compound comprising (3-aminopropyl)triethoxysilane, and
at least one second organic silicon compound selected from the group of methyltrimethoxysilane, methyltriethoxysilane, ethyltrimethoxysilane, ethyltriethoxysilane, propyltrimethoxysilane, Propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

In another highly preferred embodiment, a method is wherein the first composition comprises (A):
- at least one first organic silicon compound comprising (3-aminopropyl)triethoxysilane, and
- at least one second organic silicon compound selected from the group of methyltrimethoxysilane, methyltriethoxysilane, ethyltriethoxysilane, hexyltriethoxysilane and octyltriethoxysilane.

The corresponding hydrolysis or condensation products are, for example, the following compounds:

Hydrolysis of $C_1$-$C_6$ alkoxysilane of formula (S-I) with water (reaction scheme using 3-aminopropyltriethoxysilane as an example):

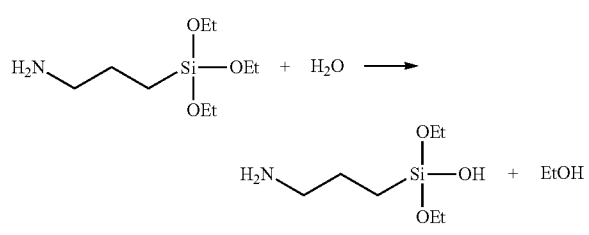

Depending on the amount of water used, the hydrolysis reaction can also take place several times per $C_1$-$C_6$ alkoxysilane used:

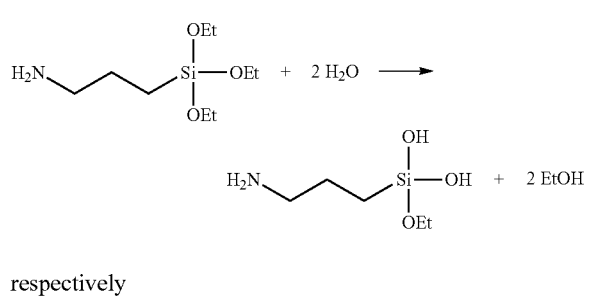

respectively

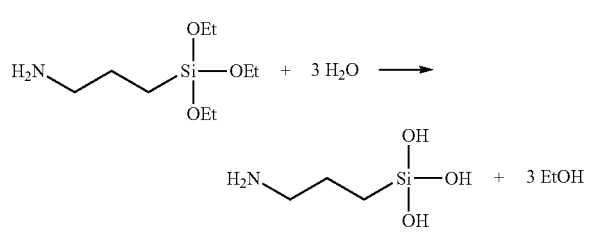

Hydrolysis of $C_1$-$C_6$ alkoxysilane of the formula (S-IV) with water (reaction scheme using methyltrimethoxysilane as an example):

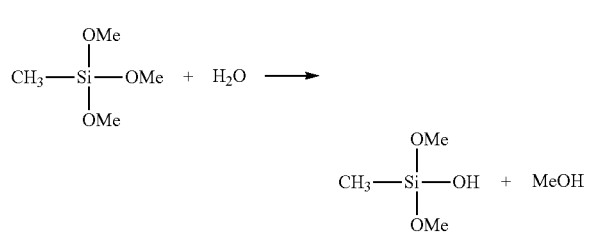

Depending on the amount of water used, the hydrolysis reaction can also take place several times per $C_1$-$C_6$ alkoxysilane used:

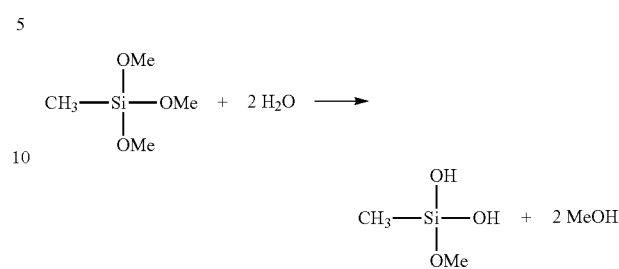

respectively

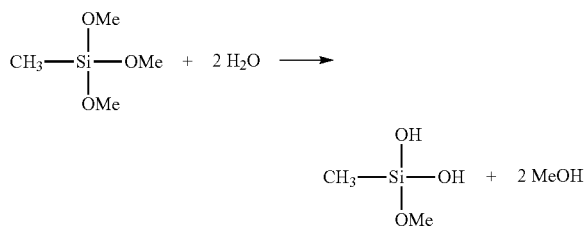

Possible condensation reactions include (shown using the mixture (3-aminopropyl)triethoxysilane and methyltrimethoxysilane):

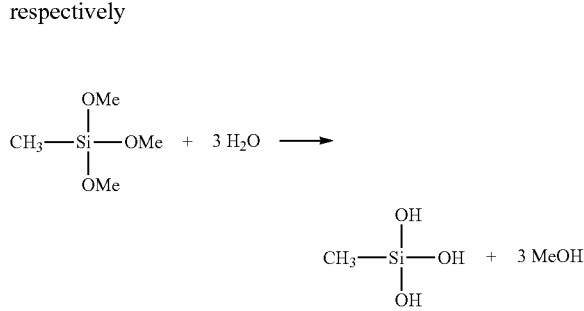

+ EtOH and/or

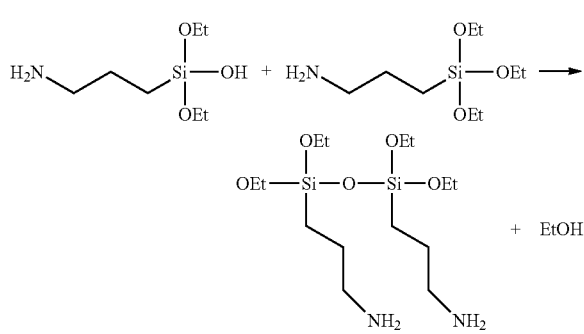

+ H2O and/or

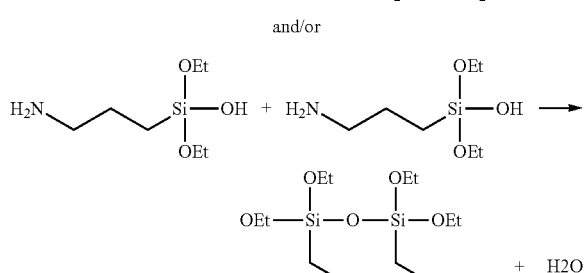

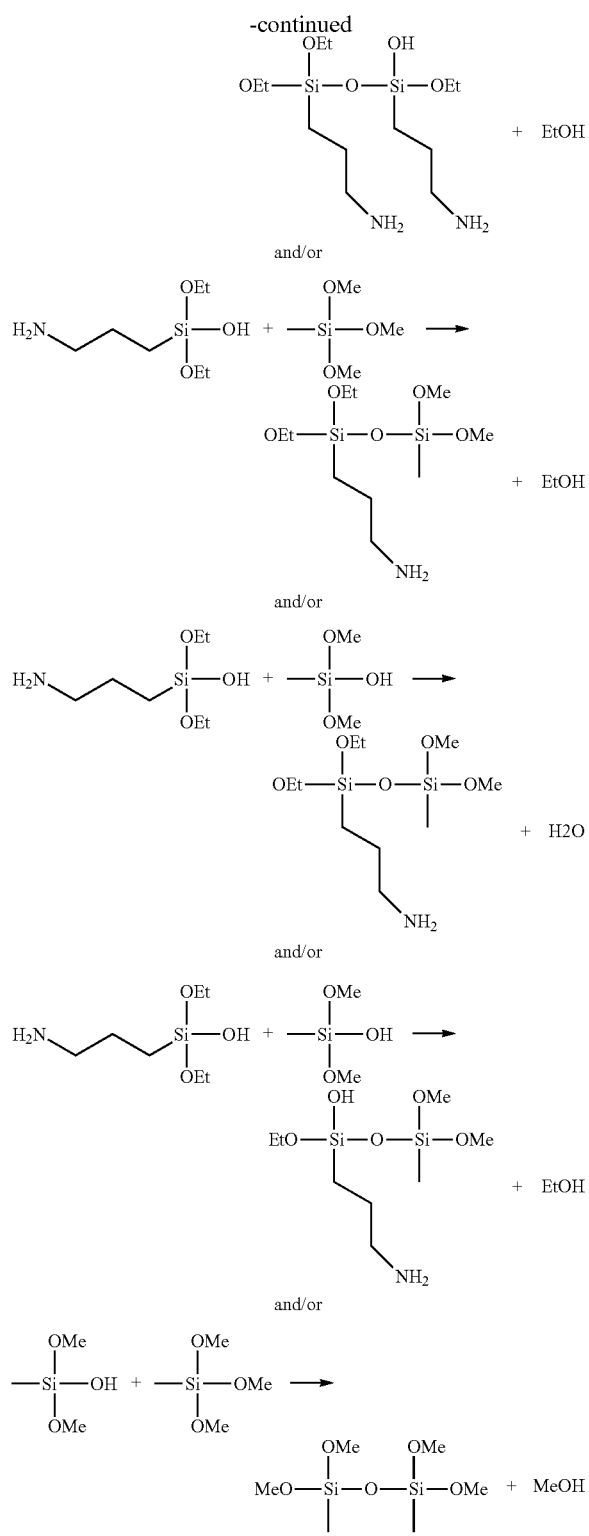

In the above exemplary reaction schemes the condensation to a dimer is shown in each case, but further condensations to oligomers with several silane atoms are also possible and also preferred.

Both partially hydrolyzed and fully hydrolyzed $C_1$-$C_6$ alkoxysilanes of the formula (S-I) can participate in these condensation reactions, which undergo condensation with as yet unreacted, partially or also fully hydrolyzed $C_1$-$C_6$ alkoxysilanes of the formula (S-I). In this case, the $C_1$-$C_6$ alkoxysilanes of formula (S-I) react with themselves.

Furthermore, both partially hydrolyzed and fully hydrolyzed $C_1$-$C_6$-alkoxysilanes of the formula (S-I) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-I) react with the $C_1$-$C_6$ alkoxysilanes of formula (S-IV).

Furthermore, both partially hydrolyzed and fully hydrolyzed $C_1$-$C_6$-alkoxysilanes of the formula (S-IV) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-IV) react with themselves.

The composition (A) as contemplated herein may contain one or more organic $C_1$-$C_6$ alkoxysilanes (A1) in various proportions. The skilled person determines this depending on the desired thickness of the silane coating on the keratin material and on the amount of keratin material to be treated.

Particularly storage-stable compositions with very good dyeing results in application could be obtained when composition (A) comprises—based on its total weight—one or more organic $C_1$-$C_6$-alkoxysilanes (A1) and/or the condensation products thereof in a total amount of about 30.0 to about 85.0 wt. %, preferably about 35.0 to about 80.0 wt. %, more preferably about 40.0 to about 75.0 wt. %, still more preferably about 45.0 to about 70.0 wt. % and very particularly preferably about 45.0 to about 70.0 wt. %, preferably from about 35.0 to about 80.0% by weight, more preferably from about 40.0 to about 75.0% by weight, still more preferably from about 45.0 to about 70.0% by weight and most preferably from about 50.0 to about 65.0% by weight.

In a further embodiment, a very particularly preferred process is wherein the first composition (A) comprises—based on the total weight of the composition (A)—one or more organic $C_1$-$C_6$ alkoxysilanes (A2) and/or the condensation products thereof in a total amount of from about 30.0 to about 85.0 wt. %, preferably from about 35.0 to about 80.0% by weight, more preferably from about 40.0 to about 75.0% by weight, still more preferably from about 45.0 to about 70.0% by weight and most preferably from about 50.0 to about 65.0% by weight.

Coloring Compounds (A2) in the Composition (A)

As a second essential component of the present disclosure, the composition (A) comprises at least one colorant compound (A2) selected from the group of pigments and direct dyes.

As contemplated herein, the colorant compound(s) will be selected from pigments, direct dyes, where direct dyes may also be photochromic dyes and thermochromic dyes.

Very preferably, the composition (A) comprises at least one pigment.

Pigments within the meaning of the present disclosure are colorant compounds which have a solubility in water at 25° C. of less than 0.5 g/L, preferably less than 0.1 g/L, still more preferably less than 0.05 g/L. Water solubility, for example, can be done using the method described below: 0.5 g of the pigment is weighed out in a beaker. A stirring bar is added. Then one liter of distilled water is added. This mixture is heated to 25° C. for one hour with stirring on a magnetic stirrer. If undissolved components of the pigment are still visible in the mixture after this period, the solubility of the pigment is below 0.5 g/L. If the pigment-water mixture cannot be assessed visually due to the high intensity of the pigment, which may be finely dispersed, the mixture is filtered. If a portion of undissolved pigment remains on the filter paper, the solubility of the pigment is below 0.5 g/L.

Suitable color pigments can be of inorganic and/or organic origin.

In a preferred embodiment, a composition as contemplated herein is wherein it comprises at least one colorant compound selected from the group of inorganic and/or organic pigments.

Preferred color pigments are selected from synthetic or natural inorganic pigments. Inorganic color pigments of natural origin can be produced, for example, from chalk, ocher, umber, green earth, burnt Terra di Siena or graphite. Furthermore, black pigments such as iron oxide black, colored pigments such as ultramarine or iron oxide red, and fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulfates, chromates and/or molybdates. Particularly preferred color pigments are black iron oxide (CI 77499), yellow iron oxide (CI 77492), red and brown iron oxide (CI 77491), manganese violet (CI 77742), ultramarines (sodium aluminum sulfosilicates, CI 77007, Pigment Blue 29), chromium oxide hydrate (CI77289), iron blue (ferric ferrocyanide, CI77510) and/or carmine (cochineal).

Colored pearlescent pigments are also particularly preferred colorants from the group of pigments as contemplated herein. These are usually mica and/or mica-based and may be coated with one or more metal oxides. Mica belongs to the layer silicates. The main representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as a pearlescent pigment. Particularly preferred pearlescent pigments are based on natural or synthetic mica and are coated with one or more of the metal oxides mentioned above. The color of the respective pigments can be varied by varying the layer thickness of the metal oxide(s).

Also preferred mica-based pigments are synthetically produced mica platelets coated with metal oxide, in particular based on synthetic fluorophlogopite (INCI: Synthetic Fluorphlogopite). The synthetic fluorophlogopite platelets are coated, for example, with tin oxide, iron oxide(s) and/or titanium dioxide. The metal oxide layers may further contain pigments such as Iron (III) hexacyanidoferrate (II/III) or carmine red. Such mica pigments are available, for example, under the name SYNCRYSTAL from Eckart.

In the context of a very particularly preferred embodiment, a process is wherein the first composition (A) comprises at least one inorganic pigment (A2) preferably selected from the group of colored metal oxides, metal hydroxides, metal oxide hydrates, silicates, metal sulfides, complex metal cyanides, metal sulfates, bronze pigments and/or mica- or mica-based colored pigments coated with at least one metal oxide and/or a metal oxychloride.

In a further preferred embodiment, the composition (A) is wherein it comprises at least one colorant compound (A2) from the group of pigments selected from the group of colored metal oxides, metal hydroxides, metal oxide hydrates, silicates, metal sulfides, complex metal cyanides, metal sulfates, bronze pigments and/or from mica- or mica-based colorant compounds coated with at least one metal oxide and/or a metal oxychloride.

In another preferred embodiment, a composition (A) is wherein it comprises at least one colorant compound (A2) selected from mica- or mica-based pigments reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

In a preferred embodiment, composition (A) is wherein it comprises at least one coloring compound selected from the group of inorganic pigments, black iron oxide (CI 77499), yellow iron oxide (CI 77492), red iron oxide (CI 77491) and mixtures thereof.

Yellow iron oxide (or iron oxide yellow) is the name for FeO(OH), in the color index under C.I. Pigment Yellow 42 listed.

Red iron oxide (or iron oxide red) is the name for $Fe_2O_3$, in the color index under C.I. Pigment Red 101 listed. Depending on the particle size, red iron oxide pigments can be adjusted to be very yellowish (small particle size) to very blueish (coarse particles).

Black iron oxide (or iron oxide black) is listed in the Color Index under C.I. Pigment Black 11 listed. Iron oxide black is ferromagnetic. The chemical formula is often given as $Fe_3O_4$, in reality there is a solid solution of $Fe_2O_3$ and FeO with inverse spinel structure. Further black pigments are obtained by doping with chromium, copper or manganese.

Brown Black Iron Oxide (or Iron Oxide Brown) usually does not refer to a defined pigment, but to a mixture of yellow, red and/or black iron oxide.

Iron oxide pigments usually have particle diameters in the range of about 2,000 to about 4,000 nm. For some applications, especially for cosmetic purposes, it may be advantageous to use iron oxide pigments with significantly smaller particle diameters. For example, hair dyes with iron oxide pigments that have a particle diameter in the range of about 100 to about 1,000 nm, more preferably about 150 nm to about 700 nm, show better durability and better gray coverage.

Even more preferred, therefore, is a composition (A) further comprising a colorant compound selected from the group of pigments and/or direct dyes, wherein the colorant compound comprises a pigment selected from the group of iron oxide pigments, and wherein the iron oxide pigment has a particle diameter in the range of about 100 to about 1,000 nm, more preferably about 150 nm to about 700 nm.

Examples of particularly suitable color pigments are commercially available under the trade names Rona®, Colorona®, Xirona®, Dichrona® and Timiron® from Merck, Ariabel® and Unipure® from Sensient, Prestige® and SynCrystal from Eckart Cosmetic Colors and Sunshine® from Sunstar.

Very particularly preferred pigments with the trade name Colorona® are, for example:
Colorona Copper, Merck, MICA, CI 77491 (IRON OXIDES)
Colorona Copper Fine, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aboriginal Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360)

Colorona Majestic Green, Merck, CI 77891 (TITANIUM DIOXIDE), MICA, CI 77288 (CHROMIUM OXIDE GREENS)

Colorona Light Blue, Merck, MICA, TITANIUM DIOXIDE (CI 77891), FERRIC FERROCYANIDE (CI 77510)

Colorona Red Gold, Merck, MICA, CI 77891 (TITANIUM DIOXIDE), CI 77491 (IRON OXIDES)

Colorona Gold Plus MP 25, Merck, MICA, TITANIUM DIOXIDE (CI 77891), IRON OXIDES (CI 77491)

Colorona Carmine Red, Merck, MICA, TITANIUM DIOXIDE, CARMINE

Colorona Blackstar Green, Merck, MICA, CI 77499 (IRON OXIDES)

Colorona Bordeaux, Merck, MICA, CI 77491 (IRON OXIDES)

Colorona Bronze, Merck, MICA, CI 77491 (IRON OXIDES)

Colorona Bronze Fine, Merck, MICA, CI 77491 (IRON OXIDES)

Colorona Fine Gold MP 20, Merck, MICA, CI 77891 (TITANIUM DIOXIDE), CI 77491 (IRON OXIDES)

Colorona Sienna Fine, Merck, CI 77491 (IRON OXIDES), MICA

Colorona Sienna, Merck, MICA, CI 77491 (IRON OXIDES)

Colorona Precious Gold, Merck, Mica, CI 77891 (Titanium dioxide), Silica, CI 77491 (Iron oxides), Tin oxide Colorona Sun Gold Sparkle MP 29, Merck, MICA, TITANIUM DIOXIDE, IRON OXIDES, MICA, CI 77891, CI 77491 (EU)

Colorona Mica Black, Merck, CI 77499 (Iron oxides), Mica, CI 77891 (Titanium dioxide)

Colorona Bright Gold, Merck, Mica, CI 77891 (Titanium dioxide), CI 77491 (Iron oxides)

Colorona Blackstar Gold, Merck, MICA, CI 77499 (IRON OXIDES)

Colorona® SynCopper, Merck, Synthetic Fluorphlogopite (and) Iron Oxides

Colorona® SynBronze, Merck, Synthetic Fluorphlogopite (and) Iron Oxides

Further particularly preferred pigments with the trade name Xirona® are, for example:

Xirona® Golden Sky, Merck, Silica, CI 77891 (Titanium Dioxide), Tin Oxide

Xirona® Caribbean Blue, Merck, Mica, CI 77891 (Titanium Dioxide), Silica, Tin Oxide Xirona® Kiwi Rose, Merck, Silica, CI 77891 (Titanium Dioxide), Tin Oxide Xirona® Magic Mauve, Merck, Silica, CI 77891 (Titanium Dioxide), Tin Oxide Xirona® Le Rouge, Merck, Iron Oxides (and) Silica In addition, particularly preferred pigments with the trade name Unipure® are, for example:

Unipure Red LC 381 EM, Sensient CI 77491 (Iron Oxides), Silica

Unipure Black LC 989 EM, Sensient, CI 77499 (Iron Oxides), Silica

Unipure Yellow LC 182 EM, Sensient, CI 77492 (Iron Oxides), Silica

Also particularly preferred pigments with the trade name Flamenco® are, for example:

Flamenco® Summit Turquoise T30D, BASF, Titanium Dioxide (and) Mica

Flamenco® Super Violet 530Z, BASF, Mica (and) Titanium Dioxide

In a further embodiment, composition (A) may also comprise one or more colorant compounds selected from the group of organic pigments The organic pigments of the present disclosure are correspondingly insoluble organic dyes or colorants which may be selected, for example, from the group comprising nitroso-, nitro-azo-, xanthene-, anthraquinone-, isoindolinone-, isoindoline-, quinacridone-, perinone-, perylene-, diketo-pyrrolopyorrole-, indigo-, thioindido-, dioxazine-, and/or triarylmethane compounds.

Particularly suitable organic pigments are, for example, carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, a method is wherein the first composition (A) comprises at least one organic pigment (A2) which is preferably selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a colored paint. As contemplated herein, the term color varnish means particles comprising a layer of absorbed dyes, the unit of particle and dye being insoluble under the above conditions. The particles may be, for example, inorganic substrates, which may be aluminum, silica, calcium borosilicate, calcium aluminum borosilicate, or aluminum.

Alizarin color varnish, for example, can be used as a color varnish.

Due to their excellent light and temperature resistance, the use of the above pigments in the composition as contemplated herein is particularly preferred. Furthermore, it is preferred if the pigments used have a certain particle size. On the one hand, this particle size leads to an even distribution of the pigments in the polymer film formed and, on the other hand, avoids a rough hair or skin feeling after application of the cosmetic product. It is therefore advantageous as contemplated herein if the at least one pigment has an average particle size $D_{50}$ of from about 1.0 to about 50 µm, preferably from about 5.0 to about 45 µm, preferably from about 10 to about 40 µm, in particular from about 14 to about 30 µm. For example, the average particle size $D_{50}$ can be determined using dynamic light scattering (DLS).

Pigments with a specific shaping may also have been used to color the keratin material. For example, a pigment based on a lamellar and/or a lenticular substrate platelet can be used. Furthermore, coloring based on a substrate platelet comprising a vacuum metallized pigment ("VMP") is also possible.

In another particularly preferred embodiment, a method is wherein the first composition (A) comprises at least one pigment (A2) selected from the group of pigments based on a lamellar substrate platelet, pigments based on a lenticular substrate platelet, and pigments based on a substrate platelet comprising a vacuum metallized pigment ("VMP").

The substrate platelets of this type have an average thickness of at most about 50 nm, preferably less than about 30 nm, particularly preferably at most about 25 nm, for example at most about 20 nm. The average thickness of the substrate platelets is at least about 1 nm, preferably at least about 2.5 nm, particularly preferably at least about 5 nm, for example at least about 10 nm. Preferred ranges for substrate wafer thickness are about 2.5 to about 50 nm, about 5 to about 50 nm, about 10 to about 50 nm; about 2.5 to about 30 nm, about 5 to about 30 nm, about 10 to about 30 nm; about 2.5 to about 25 nm, about 5 to about 25 nm, about 10 to about 25 nm, about 2.5 to about 20 nm, about 5 to about 20 nm, and about 10 to about 20 nm. Preferably, each substrate plate has a thickness that is as uniform as possible.

Due to the low thickness of the substrate platelets, the pigment exhibits particularly high hiding power.

The substrate plates have a monolithic structure. Monolithic in this context means comprising a single self-included unit without fractures, stratifications or inclusions, although structural changes may occur within the substrate platelets. The substrate platelets are preferably homogeneous in structure, i.e. no concentration gradient occurs within the platelets. In particular, the substrate platelets are not layered and do not have particles or particulates distributed therein.

The size of the substrate platelet can be adapted to the respective application purpose, in particular the desired effect on the keratinous material. Typically, the substrate platelets have an average largest diameter of about 2 to 200 µm, especially about 5 to 100 µm.

In a preferred embodiment, the shape factor (aspect ratio), expressed by the ratio of the average size to the average thickness, is at least about 80, preferably at least about 200, more preferably at least about 500, especially preferably more than about 750. Here, the average size of the uncoated substrate platelets is understood to be the d50 value of the uncoated substrate platelets. Unless otherwise stated, the d50 value was determined using a Sympatec Helos instrument with Quixel wet dispersion. For sample preparation, the sample to be analyzed was predispersed in isopropanol for a period of about 3 minutes.

The substrate platelets can be composed of any material that can be formed into platelet shape.

They can be of natural origin, but also synthetically produced. Materials from which the substrate platelets can be constructed include metals and metal alloys, metal oxides, preferably aluminum oxide, inorganic compounds and minerals such as mica and (semi-)precious stones, and plastics. Preferably, the substrate platelets are constructed of metal (alloy).

Any metal suitable for metallic luster pigments can be used. Such metals include iron and steel, as well as all air- and water-resistant (semi)metals such as platinum, zinc, chromium, molybdenum and silicon, as well as their alloys such as aluminum bronzes and brass. Preferred metals are aluminum, copper, silver and gold. Preferred substrate platelets include aluminum platelets and brass platelets, with aluminum substrate platelets being particularly preferred.

Lamellar substrate platelets are exemplified by an irregularly structured edge and are also referred to as "cornflakes" due to their appearance.

Due to their irregular structure, pigments based on lamellar substrate platelets generate a high proportion of scattered light. In addition, pigments based on lamellar substrate platelets do not completely cover the existing color of a keratinous material, and effects analogous to natural graying can be achieved, for example.

Lenticular (=lens-shaped) substrate platelets have an essentially regular round edge and are also called "silverdollars" due to their appearance. Due to their regular structure, pigments based on lenticular substrate platelets have a predominance of reflected light.

Vacuum metallized pigments (VMP) can be obtained, for example, by releasing metals, metal alloys or metal oxides from suitably coated films. They are exemplified by a particularly low thickness of the substrate platelets in the range of about 5 to about 50 nm and by a particularly smooth surface with increased reflectivity. Substrate platelets comprising a vacuum metallized pigment are also referred to as VMP substrate platelets in the context of this application. VMP substrate platelets made of aluminum can be obtained, for example, by releasing aluminum from metallized foils.

The metal or metal alloy substrate plates can be passivated, for example by anodizing (oxide layer) or chromating.

Uncoated lamellar, lenticular, and/or VPM substrate plates, especially those made of metal or metal alloy, reflect incident light to a high degree and produce a light-dark flop but no color impression.

A color impression can be created, for example, due to optical interference effects. Such pigments may be based on at least single-coated substrate platelets. These show interference effects due to superposition of differently refracted and reflected light rays.

Accordingly, preferred pigments, pigments based on a coated substrate platelet. The substrate wafer preferably has at least one coating B of a highly refractive metal oxide having a coating thickness of at least about 50 nm. There is preferably another coating A between the coating B and the surface of the substrate wafer. If necessary, there is a further coating C on the layer B, which is different from the layer B underneath.

Suitable materials for coatings A, B and C are all substances that can be applied to the substrate platelets in a film-like and permanent manner and, in the case of coatings A and B, have the required optical properties. Generally, coating part of the surface of the substrate platelets is sufficient to obtain a pigment with a glossy effect. For example, only the top and/or bottom of the substrate platelets may be coated, with the side surface(s) omitted. Preferably, the entire surface of the optionally passivated substrate platelets, including the side surfaces, is covered by coating B. The substrate platelets are thus completely enveloped by coating B. This improves the optical properties of the pigment and increases its mechanical and chemical resistance. The above also applies to layer A and preferably also to layer C, if present.

Although multiple coatings A, B and/or C may be present in each case, the coated substrate wafers preferably have only one coating A, B and, if present, C in each case.

The coating B is composed of at least one highly refractive metal oxide. Highly refractive materials have a refractive index of at least about 1.9, preferably at least about 2.0, and more preferably at least about 2.4. Preferably, the coating B comprises at least about 95 wt %, more preferably at least about 99 wt %, of high refractive index metal oxide(s).

The coating B has a thickness of at least about 50 nm. Preferably, the thickness of coating B is no more than about 400 nm, more preferably no more than about 300 nm.

Highly refractive metal oxides suitable for coating B are preferably selectively light-absorbing (i.e. colored) metal oxides, such as iron(III) oxide (α- and γ-$Fe_2O_3$, red), cobalt (II) oxide (blue), chromium(III) oxide (green), titanium(III) oxide (blue, usually present in admixture with titanium oxynitrides and titanium nitrides) and vanadium (V) oxide (orange), and mixtures thereof. Colorless high-index oxides such as titanium dioxide and/or zirconium oxide are also suitable.

Coating B may contain a selectively absorbing dye, preferably about 0.001 to about 5% by weight, particularly preferably about 0.01 to about 1% by weight, in each case based on the total amount of coating B. Suitable dyes are organic and inorganic dyes which can be stably incorporated into a metal oxide coating.

The coating A preferably has at least one low refractive index metal oxide and/or metal oxide hydrate. Preferably, coating A comprises at least about 95 wt %, more preferably at least about 99 wt %, of low refractive index metal oxide (hydrate). Low refractive index materials have a refractive index of about 1.8 or less, preferably about 1.6 or less.

Low refractive index metal oxides suitable for coating A include, for example, silicon (di)oxide, silicon oxide hydrate, aluminum oxide, aluminum oxide hydrate, boron oxide, germanium oxide, manganese oxide, magnesium oxide, and mixtures thereof, with silicon dioxide being preferred. The coating A preferably has a thickness of about 1 to about 100 nm, particularly preferably about 5 to about 50 nm, especially preferably about 5 to about 20 nm.

Preferably, the distance between the surface of the substrate platelets and the inner surface of coating B is at most about 100 nm, particularly preferably at most about 50 nm, especially preferably at most 20 nm. By ensuring that the thickness of coating A, and thus the distance between the surface of the substrate platelets and coating B, is within the range specified above, it is possible to ensure that the pigments have a high hiding power.

If the pigment based on a substrate platelet has only one layer A, it is preferred that the pigment has a substrate platelet of aluminum and a layer A of silica. If the pigment based on a substrate platelet has a layer A and a layer B, it is preferred that the pigment has a substrate platelet of aluminum, a layer A of silica and a layer B of iron oxide.

As an alternative to a metal oxide, layer B may comprise a metal particle support layer having metal particles deposited on the surface of the metal particle support layer. In a preferred embodiment, the metal particles directly cover a portion of the metal particle support layer. In this embodiment, the effect pigment has areas where there are no metal particles, i.e. areas that are not covered with the metal particles.

The metal particle support layer comprise a metal layer and/or a metal oxide layer.

When the metal particle support layer comprises a metal layer and a metal oxide layer, the arrangement of these layers is not limited.

It is preferred that the metal particle support layer comprises at least one metal layer. It is further preferred that the metal layer comprises an element selected from tin (Sn), palladium (Pd), platinum (Pt) and gold (Au).

The metal layer can be formed, for example, by adding alkali to a metal salt solution comprising the metal.

If the metal particle support layer comprises a metal oxide layer, it preferably does not comprise silica. The metal oxide layer preferably comprises an oxide of at least one element selected from the group of Mg (magnesium), Sn (tin), Zn (zinc), Co (cobalt), Ni (nickel), Fe (iron), Zr (zirconium), Ti (titanium), and Ce (cerium). Particularly preferably, the metal particle support layer iii) in the form of a metal oxide layer comprises a metal oxide of Sn, Zn, Ti and Ce.

The metal particle support layer in the form of a metal oxide layer can be prepared, for example, by hydrolyzing an alkoxide of a metal that forms the metal of the metal oxide in a sol-gel process.

The thickness of the metal layer is preferably not more than 30 nm.

The metal particles may comprise at least one element selected from the group of aluminum (Al), titanium (Ti), chromium (Cr), iron (Fe), cobalt (Co), nickel (Ni), copper (Cu), zinc (Zn), ruthenium (Ru), rhodium (Rh), palladium (Pd), silver (Ag), tin (Sn), platinum (Pt), gold (Au), and alloys thereof. It is particularly preferred that the metal particles comprise at least one element selected from copper (Cu), nickel (Ni) and silver (Ag).

The average particle diameter of the metal particles is preferably not more than 50 nm, more preferably not more than 30 nm. The distance between the metal particles is preferably not more than 10 nm.

Suitable methods for forming the metal particles include vacuum evaporation, sputtering, chemical vapor deposition (CVD), electroless plating, or the like. Of these processes, electroless plating is particularly preferred.

According to a preferred embodiment, the pigments have a further coating C of a metal oxide (hydrate), which is different from the underlying coating B. Suitable metal oxides include silicon (di)oxide, silicon oxide hydrate, aluminum oxide, aluminum oxide hydrate, zinc oxide, tin oxide, titanium dioxide, zirconium oxide, iron (III) oxide, and chromium (III) oxide. Preferred is silicon dioxide.

The coating C preferably has a thickness of 10 to 500 nm, more preferably 50 to 300 nm. By providing coating C, for example based on $TiO_2$, better interference can be achieved while maintaining high hiding power.

Layers A and C serve in particular as corrosion protection as well as chemical and physical stabilization. Particularly preferred layers A and C are silica or alumina applied by the sol-gel process. This process comprises dispersing the uncoated substrate wafer or the substrate wafer already coated with layer A and/or layer B in a solution of a metal alkoxide such as tetraethyl orthosilicate or aluminum triisopropanolate (usually in a solution of organic solvent or a mixture of organic solvent and water with at least about 50 wt % organic solvent such as a C1 to C4 alcohol), and adding a weak base or acid to hydrolyze the metal alkoxide, thereby forming a film of the metal oxide on the surface of the (coated) substrate platelets.

Layer B can be produced, for example, by hydrolytic decomposition of one or more organic metal compounds and/or by precipitation of one or more dissolved metal salts, as well as any subsequent post-treatment (for example, transfer of a formed hydroxide-comprising layer to the oxide layers by annealing).

Although each of the coatings A, B and/or C may be composed of a mixture of two or more metal oxide(hydrate)s, each of the coatings is preferably composed of one metal oxide(hydrate).

The pigments based on coated lamellar or lenticular substrate platelets or the pigments based on coated VMP substrate platelets preferably have a thickness of about 70 to about 500 nm, particularly preferably about 100 to about 400 nm, especially preferably about 150 to about 320 nm, for example about 180 to about 290 nm. Due to the low thickness of the substrate platelets, the pigment exhibits particularly high hiding power. The low thickness of the coated substrate platelets is achieved in particular by keeping the thickness of the uncoated substrate platelets low, but also by adjusting the thicknesses of the coatings A and, if present, C to as small a value as possible. The thickness of coating B determines the color impression of the pigment.

Also suitable pigments are pigments based on a substrate platelet comprising artificial mica. Particularly preferred are pigments comprising α) a substrate platelet comprising artificial mica, and β) a coating comprising at least a first metal oxide (hydrate) layer comprising $TiO_2$, $SnO_2$ and/or iron oxide(s).

The adhesion and friction resistance of pigments based on coated substrate platelets in keratinic material can be significantly increased by additionally modifying the outermost layer, layer A, B or C depending on the structure, with organic compounds such as silanes, phosphoric acid esters, titanates, borates or carboxylic acids. In this case, the organic compounds are bonded to the surface of the outermost, preferably metal oxide-comprising, layer A, B, or C. The outermost layer denotes the layer that is spatially farthest from the substrate platelet. The organic compounds are preferably functional silane compounds that can bind to the metal oxide-comprising layer A, B, or C. These can be either mono- or bifunctional compounds. Examples of bifunctional organic compounds include methacryloxypropenyltrimethoxysilane, 3-methacryloxypropyltrimethoxysilane, 3-acryloxypropyltrimethoxysilane, 2-acryloxyethyltrimethoxysilane, 3-methacryloxy-propyltriethoxysilane, 3-acryloxypropyltrimethoxysilane, 2-methacryloxyethyl-triethoxysilane, 2-acryloxyethyltriethoxysilane, 3-methacryloxypropyltris(methoxyethoxy)silane, 3-methacryloxypropyltris(butoxyethoxy)silane, 3-methacryloxy-propyltris(propoxy)silane, 3-methacryloxypropyltris(butoxy)silane, 3-acryloxy-propyltris(methoxyethoxy)silane, 3-acryloxypropyltris(butoxyethoxy)silane, 3-acryloxypropyltris(butoxy)silane, vinyltrimethoxysilane, Vinyltriethoxysilane, vinylethyl dichlorosilane, vinylmethyldiacetoxysilane, vinylmethyldichlorosilane, vinylmethyldiethoxysilane, vinyltriacetoxysilane, vinyltrichlorosilane, phenylvinyldiethoxysilane, or phenylallyldichlorosilane. Furthermore, a modification with a monofunctional silane, in particular an alkylsilane or arylsilane, can be carried out. This has only one functional group, which can covalently bond to the surface pigment based on coated substrate platelets (i.e. to the outermost metal oxide-comprising layer) or, if not completely covered, to the metal surface. The hydrocarbon residue of the silane points away from the pigment. Depending on the type and nature of the hydrocarbon residue of the silane, a different degree of hydrophobicity of the pigment is achieved. Examples of such silanes include hexadecyltrimethoxysilane, propyltrimethoxysilane, etc. Particularly preferred are pigments based on silica-coated aluminum substrate platelets surface-modified with a monofunctional silane. Octyltrimethoxysilane, octyltriethoxysilane, hecadecyltrimethoxysilane and hecadecyltriethoxysilane are particularly preferred. Due to the changed surface properties/hydrophobization, an improvement can be achieved in terms of adhesion, friction resistance and alignment in the application.

Suitable pigments based on a substrate platelet include, for example, the pigments of the VISIONAIRE series from Eckart.

Pigments based on a lenticular substrate platelet are available, for example, under the name Alegrace® Gorgeous from the company Schlenk Metallic Pigments GmbH.

Pigments based on a substrate platelet comprising a vacuum metallized pigment are available, for example, under the name Alegrace® Marvelous or Alegrace® Aurous from the company Schlenk Metallic Pigments GmbH.

In the context of a further embodiment, a process is wherein the composition (A) comprises—based on the total weight of the composition (A)—one or more pigments in a total amount of from 0.001 to 20% by weight, in particular from 0.05 to 5% by weight.

As coloring compounds, the compositions (A) may also contain one or more direct dyes. Direct-acting dyes are dyes that draw directly onto the hair and do not require an oxidative process to form the color. Direct dyes are usually nitrophenylenediamines, nitroaminophenols, azo dyes, anthraquinones, triarylmethane dyes or indophenols.

The direct dyes according to the present disclosure have a solubility in water (760 mmHg) at 25° C. of more than 0.5 g/L and are therefore not to be regarded as pigments. Preferably, the direct dyes according to the present disclosure have a solubility in water (760 mmHg) at 25° C. of more than 1.0 g/L. Particularly preferably, the direct dyes according to the present disclosure have a solubility in water (760 mmHg) at 25° C. of greater than 1.5 g/L.

Direct dyes can be divided into anionic, cationic and nonionic direct dyes.

In a further preferred embodiment, a composition (A) is wherein it comprises at least one anionic, cationic and/or nonionic direct dye as the coloring compound.

In a further preferred embodiment, a process is wherein the composition (A) comprises at least one colorant compound selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

Examples of nonionic direct dyes that can be used are nonionic nitro and quinone dyes and neutral azo dyes. Suitable nonionic direct dyes are those available under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

Anionic direct dyes are also called acid dyes. Acid dyes are direct dyes that have at least one carboxylic acid moiety (—COOH) and/or one sulfonic acid moiety (—SO$_3$H). Depending on the pH, the protonated forms (—COOH, —SO$_3$H) of the carboxylic or sulfonic acid moieties are in equilibrium with their deprotonated forms (—COO$^-$, —SO$_3^-$ present). As pH decreases, the proportion of protonated forms increases. If direct dyes are used in the form of their salts, the carboxylic acid groups or sulfonic acid groups are present in deprotonated form and are neutralized with corresponding stoichiometric equivalents of cations to maintain electroneutrality. Acid dyes as contemplated herein can also be used in the form of their sodium salts and/or their potassium salts.

The acid dyes according to the present disclosure have a solubility in water (760 mmHg) at 25° C. of more than 0.5 g/L and are therefore not to be considered pigments. Preferably, the acid dyes according to the present disclosure have a solubility in water (760 mmHg) at 25° C. of greater than 1.0 g/L.

The alkaline earth salts (such as calcium salts and magnesium salts) or aluminum salts of acid dyes often have poorer solubility than the corresponding alkali salts. If the solubility of these salts is below 0.5 g/L (25° C., 760 mmHg), they do not fall under the definition of a direct dye.

A key feature of acid dyes is their ability to form anionic charges, with the carboxylic or sulfonic acid groups responsible for this usually being attached to various chromophoric systems. Suitable chromophoric systems are found, for example, in the structures of nitrophenylenediamines, nitroaminophenols, azo dyes, anthraquinone dyes, triarylmethane dyes, xanthene dyes, rhodamine dyes, oxazine dyes, and/or indophenol dyes.

For example, one or more compounds from the following group can be selected as particularly well-suited acid dyes: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C Red 46, True Red D, FD&C Red No. 2, Food Red 9, Naphthol Red S), Acid Red 33 (Red 33, Fuchsia Red, D&C Red 33, CI 17200), Acid Red 35 (CI C.I.18065), Acid Red 51 (CI 45430, Pyrosine B, Tetraiodofluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The water solubility of anionic direct dyes can be determined, for example, in the following way. 0.1 g of the anionic direct dye is added to a beaker. A stirring bar is added. Then 100 ml of water is added. This mixture is heated to 25° C. on a magnetic stirrer while stirring. It is stirred for 60 minutes. The aqueous mixture is then visually assessed. If undissolved residues are still present, the amount of water is increased—for example in steps of 10 ml. Water is added until the amount of dye used has completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml of water at 25° C., the solubility of the dye is 1.0 g/L.

Acid Yellow 1 is named 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3 (2H)-dione and has a water solubility of 20 g/L (25° C.).

Acid Yellow 9 is the disodium salt of 8-hydroxy-5,7-dinitro-2-naphthalenesulfonic acid, and its water solubility is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and readily soluble in water at 25° C.

Acid Orange 7 is the sodium salt of 4-[(2-hydroxy-1-naphthyl)azo]benzenesulfonate. Its solubility in water is more than 7 g/L (25° C.).

Acid Red 18 is the trisodium salt of 7-hydroxy-8-[(E)-(4-sulfonato-1-naphthyl)-diazenyl)]-1,3-naphthalenedisulfonate and has a very high water solubility of more than 20% by weight.

Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is reported to be greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a water solubility greater than 20% by weight (25° C.).

Thermochromic dyes can also be used. Thermochromism involves the property of a material to reversibly or irreversibly change its color as a function of temperature. This can be done by changing both the intensity and/or the wavelength maximum.

Finally, it is also possible to use photochromic dyes. Photochromism involves the property of a material to reversibly or irreversibly change its color depending on irradiation with light, especially UV light. This can be done by changing both the intensity and/or the wavelength maximum.

In the context of a further embodiment, a process is wherein the composition (A) comprises—based on the total weight of the composition (A)—one or more direct dyes in a total amount of from about 0.001 to about 20% by weight, in particular from about 0.05 to about 5% by weight.

Other Cosmetic Ingredients in the Composition (A)

In addition, the composition (A) may also contain one or more other cosmetic ingredients.

The cosmetic ingredients that may be optionally used in the composition (A) may be any suitable ingredients to impart further beneficial properties to the composition. For example, in the composition (A), a solvent, a thickening or film-forming polymer, a surface-active compound from the group of nonionic, cationic, anionic or zwitterionic/amphoteric surfactants, the coloring compounds from the group of pigments, the direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

The selection of these other substances will be made by the skilled person according to the desired properties of the agents. With regard to further optional components as well as the quantities of these components used, reference is expressly made to the relevant manuals known to the skilled person.

In the preparation of the composition (A), the at least one colorant compound (A2) selected from the group of pigments and direct dyes is preferably used in the form of a pigment suspension comprising the at least one colorant compound (A2) and a liquid carrier medium. The carrier medium is preferably non-aqueous. The carrier medium may include, for example, a silicone oil. Accordingly, the composition (A) comprises the liquid carrier medium in addition to the two ingredients (A1) and (A2) essential to the present disclosure.

Water Content (A1) in the Composition (A)

The method is exemplified by the application of a first composition (A) to the keratinous material.

In the context of the present disclosure, composition (A) means a ready-to-use composition which, in its present embodiment, can be applied to keratin materials, in particular to hair.

In the process, the composition (A) can be provided either as-is in a container. However, with the $C_1$-$C_6$ alkoxysilanes, the composition (A) comprises very reactive compounds. However, to avoid problems related to storage stability, it is particularly preferred to prepare the ready-to-use and reactive composition (A) just before use by mixing two or more storage-stable compositions. For example, the ready-to-use composition (A) can be prepared by mixing a low-water silane blend (A'), which comprises the organic $C_1$-$C_6$ alkoxysilane(s) (A1) in concentrated form, and a high-water carrier formulation (A''), which can be, for example, a gel, a lotion or a surfactant system.

Accordingly, the ready-to-use composition (A) preferably has a higher water content, which—based on the total weight of the composition (A)—may be in the range from about 50.0 to about 90.0% by weight, preferably from about 55.0 to about 90.0% by weight, further preferably from about 60.0 to about 90.0% by weight and particularly preferably from about 70.0 to about 90.0% by weight.

In the context of a further embodiment, a process is wherein the composition (A) comprises—based on the total weight of the composition (A)—from about 50.0 to about 90.0% by weight, preferably from about 55.0 to about 90.0% by weight, further preferably from about 60.0 to about 90.0% by weight and particularly preferably from about 70.0 to about 90.0% by weight of water.

pH Value of the Compositions (A)

In further experiments it has been found that the pH values of composition (A) can have an influence on the color intensities obtained during dyeing. It was found that alkaline pH values in particular have a beneficial effect on the dyeing performance achievable in the process.

For this reason, it is preferred that the compositions (A) have a pH of from about 7.0 to about 12.0, preferably from about 7.5 to about 11.5, more preferably from about 8.0 to about 11.0, and most preferably from about 8.0 to about 10.5.

The pH value can be measured using the usual methods known from the state of the art, such as pH measurement using glass electrodes via combination electrodes or using pH indicator paper.

In another very particularly preferred embodiment, a process wherein the composition (A) has a pH of from about 7.0 to about 12.0, preferably from about 7.5 to about 11.5, more preferably from about 8.0 to about 11.0, and most preferably from about 8.0 to about 10.5.

Tannic Acid (B1) in Composition (B)

Composition (B) comprises tannic acid as an essential ingredient of the present disclosure.

Tannic acid, also known as tannic acid or tannin, is a chemically non-uniform substance from the group of tannins. Characteristic is the polyphenolic structure. Tannic acid does not contain a carboxylic acid group.

Tannic acid is a mixture of esters of glucose with gallic acid and 3-galloyl gallic acid.

A preferred method is wherein the composition (B) comprises—based on the total weight of the composition (B)—from about 0.1 to about 20% by weight and more preferably from about 0.5 to about 10% by weight of tannic acid.

Without wishing to be bound by this theory, it is assumed that the tannic acid, when applied to keratinous material previously treated with composition (A), leads to greater crosslinking of the film formed on the keratinous material by the alkoxysilanes and/or their hydrolysis or condensation products, thereby increasing the wash resistance and/or the friction resistance of the dyeings obtained.

Water in the Composition (B)

Tannic acid is in powder form and is preferably used in the form of an aqueous solution. Accordingly, the composition (B) preferably further comprises water.

Accordingly, a preferred method is wherein the composition (B) comprises—based on the total weight of the composition (B)—from about 60 to about 99.9% by weight, preferably from about 80 to about 99.5% by weight, and further preferably from about 85 to about 99% by weight of water.

pH Value of the Compositions (B)

In further experiments, it has been found that the pH values of composition (B) can have an influence on the fastnesses obtained during dyeing. It was found that alkaline pH values in particular have a beneficial effect on the fastness that can be achieved in the process.

For this reason, it is preferred that the compositions (B) have a pH of from about 7 to about 12.7, preferably from about 7.5 to about 12 more preferably from about 8 to about 11.5 and most preferably from about 9 to about 11.

The pH value can be measured using the usual methods known from the state of the art, such as pH measurement using glass electrodes via combination electrodes or using pH indicator paper.

In another very particularly preferred embodiment, a process wherein the composition (B) has a pH of from about 7 to about 12.7, preferably from about 7.5 to about 12 more preferably from about 8 to about 11.5 and most preferably from about 9 to about 11.

Acidifying agents and/or alkalizing agents in particular can be used to adjust the above pH values.

Particularly preferably, composition (B) further comprises ascorbic acid.

Accordingly, a preferred method is wherein the composition (B) further comprises—based on the total weight of the composition (B)—from about 0.1 to about 20% by weight and more preferably from about 0.1 to about 5% by weight of ascorbic acid.

Alternatively, or in addition to ascorbic acid, the composition may include an antioxidant such as tocopherol, butylated hydroxyanisole (BHA), and/or butylated hydroxytoluene (BHT).

Film-Forming Polymers in the Composition (B)

The composition (B) may further additionally comprise at least one film-forming polymer Polymers are understood to be macromolecules with a molecular weight of at least 1000 g/mol, preferably of at least 2500 g/mol, particularly preferably of at least 5000 g/mol, which include identical, repeating organic units. The polymers of the present disclosure may be synthetically produced polymers prepared by polymerizing one type of monomer or by polymerizing different types of monomers that are structurally different from each other. If the polymer is produced by polymerization of a monomer type, it is referred to as homo-polymers. If structurally different monomer types are used in the polymerization, the resulting polymer is called a copolymer.

The maximum molecular weight of the polymer depends on the degree of polymerization (number of polymerized monomers) and the batch size, and is partly determined by the polymerization method. In terms of the present disclosure, it is preferred if the maximum molecular weight of the film-forming hydrophobic polymer is not more than $10^7$ g/mol, preferably not more than $10^6$ g/mol, and particularly preferably not more than $10^5$ g/mol.

For the purposes of the present disclosure, a film-forming polymer is understood to be a polymer capable of forming a film on a substrate, for example on a keratinous material or a keratinous fiber. The formation of a film can be demonstrated, for example, by viewing the polymer-treated keratin material under a microscope.

In the context of a further preferred embodiment, a method is wherein the second composition (B) comprises at least one film-forming polymer.

In the context of another particularly preferred embodiment, a process is wherein the second composition (B) comprises at least one film-forming polymer preferably selected from the group of homopolymers or copolymers of acrylic acid, methacrylic acid, acrylic esters, methacrylic esters, acrylic amides, methacrylic amides, vinylpyrrolidone, vinyl alcohol, vinyl acetate, ethylene, propylene, styrene, polyurethanes, polyesters and/or polyamides.

The film-forming polymers can be hydrophilic or hydrophobic.

In a first embodiment, it may be preferred to use in the composition (B), at least one hydrophobic film-forming polymer.

A hydrophobic polymer is defined as a polymer that has a solubility in water at 25° C. (760 mmHg) of less than 1% by weight.

For example, the water solubility of the film-forming hydrophobic polymer can be determined in the following way. 1.0 g of the polymer is added to a beaker. Make up to 100 g with water. A stirring bar is added and the mixture is heated to 25° C. on a magnetic stirrer with stirring. It is stirred for 60 minutes. The aqueous mixture is then visually assessed. If the polymer-water mixture cannot be visually assessed due to high turbidity of the mixture, the mixture is filtered. If a portion of undissolved polymer remains on the filter paper, then the solubility of the polymer is less than 1% by weight.

In particular, the polymers of the acrylic acid type, the polyurethanes, the polyesters, the polyamides, the polyureas, the cellulose polymers, the nitrocellulose polymers, the silicone polymers, the polymers of the acrylamide type and the polyisoprenes can be mentioned here.

Particularly suitable film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In another preferred embodiment, a composition (B) is wherein it comprises at least one film-forming hydrophobic polymer selected from the group of the copolymers of acrylic acid, the copolymers of methacrylic acid, the homopolymers or copolymers of acrylic acid esters, the homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming hydrophobic polymers selected from the group of synthetic polymers, polymers obtainable by free-radical polymerization or natural polymers have proved particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters or amides of (meth)acrylic acid having at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth)acrylate, isononyl (meth)acrylate, 2-ethylhexyl (meth)acrylate, lauryl (meth)acrylate), isopentyl (meth)acrylate, n-butyl (meth)acrylate), Isobutyl (meth)acrylate, ethyl (meth)acrylate, methyl (meth)acrylate, tert-butyl (meth) acrylate, stearyl (meth)acrylate, hydroxyethyl (meth)acrylate, 2-hydroxypropyl (meth)acrylate, 3-hydroxypropyl (meth)acrylate and/or mixtures thereof.

Further film-forming hydrophobic polymers can be selected from the homo- or copolymers of (meth)acrylamide, N-alkyl-(meth)acrylamides, in particular those with $C_2$-$C_{18}$ alkyl groups, such as N-ethyl-acrylamide, N-tert-butyl-acrylamide, le N-octylacrylamide, N-di(C1-C4)alkyl-(meth)acrylamide.

Other preferred anionic copolymers are, for example, copolymers of acrylic acid, methacrylic acid or their $C_1$-$C_6$ alkyl esters, as sold under the INCI declaration Acrylates Copolymers. A suitable commercial product is, for example, Aculyn® 33 from Rohm & Haas. However, copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are in particular acrylic acid, methacrylic acid and itaconic acid; suitable alkoxylated fatty alcohols are in particular steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001® (Acrylates/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohm und Haas distributed Soltex OPT (Acrylates/C12-22 Alkyl methacrylate Copolymer).

Suitable polymers based on vinyl monomers may include, for example, the homopolymers and copolymers of N-vinylpyrrolidone, vinylcaprolactam, vinyl-(C1-C6)alkyl-pyrrole, vinyl oxazole, vinyl thiazole, vinyl pyrimidine, vinyl imidazole.

Also particularly suitable are the copolymers octylacrylamide/acrylates/butylaminoethyl methacrylate copolymer, such as those sold commercially by NATIONAL STARCH under the trade names AMPHOMER® or LOVOCRYL® 47, or the copolymers of acrylates/octylacrylamides sold under the trade names DERMACRYL® LT and DERMACRYL® 79 by NATIONAL STARCH.

Suitable polymers based on olefins include, for example, the homopolymers and copolymers of ethylene, propylene, butene, isoprene and butadiene.

In another embodiment, the film-forming hydrophobic polymers may be the block copolymers comprising at least one block of styrene or the derivatives of styrene. These block copolymers may be copolymers comprising one or more blocks in addition to a styrene block, such as styrene/ethylene, styrene/ethylene/butylene, styrene/butylene, styrene/isoprene, styrene/butadiene. Corresponding polymers are sold commercially by BASF under the trade name "Luvitol HSB".

Intense, friction-resistant and washfast colorations could be obtained when the composition (B) included at least one film-forming polymer selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, a process is wherein the composition (B) comprises at least one film-forming polymer selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may be preferred to use at least one hydrophilic film-forming polymer in the composition (B).

By a hydrophilic polymer is meant a polymer that has a solubility in water at 25° C. (760 mmHg) of more than 1% by weight, preferably more than 2% by weight.

The water solubility of the film-forming hydrophilic polymer can be determined, for example, in the following way. 1.0 g of the polymer is added to a beaker. Make up to 100 g with water. A stirring bar is added and the mixture is heated to 25° C. on a magnetic stirrer with stirring. It is stirred for 60 minutes. The aqueous mixture is then visually assessed. A completely dissolved polymer appears macroscopically homogeneous. If the polymer-water mixture cannot be visually assessed due to high turbidity of the mixture, the mixture is filtered. If no undissolved polymer remains on the filter paper, then the solubility of the polymer is greater than 1% by weight.

Nonionic, anionic and cationic polymers can be used as film-forming, hydrophilic polymers.

Suitable film-forming, hydrophilic polymers can be selected, for example, from the group of polyvinylpyrrolidone (co)polymers, polyvinyl alcohol (co)polymers, vinyl acetate (co)polymers, the carboxyvinyl (co)polymers, the acrylic acid (co)polymers, the methacrylic acid (co)polymers, the natural gums, the polysaccharides and/or the acrylamide (co)polymers.

Furthermore, it is particularly preferred to use polyvinylpyrrolidone (PVP) and/or a vinylpyrrolidone-comprising copolymer as the film-forming hydrophilic polymer.

In another very particularly preferred embodiment, a composition (B) is wherein it comprises at least one film-forming hydrophilic polymer selected from the group of polyvinylpyrrolidone (PVP) and the copolymers of polyvinylpyrrolidone.

It is further preferred if the composition (B) comprises polyvinylpyrrolidone (PVP) as the film-forming hydrophilic polymer. Surprisingly, the wash fastness of the dyes obtained with PVP-comprising agents (b9 was also very good).

Particularly well-suited polyvinylpyrrolidones are available, for example, under the name Luviskol® K from BASF SE, especially Luviskol® K 90 or Luviskol® K 85 from BASF SE.

Another explicitly very suitable polyvinylpyrrolidone (PVP) can be the polymer PVP K30, which is marketed by the company Ashland (ISP, POI Chemical). PVP K 30 is a polyvinylpyrrolidone that is very soluble in cold water and has the CAS number 9003-39-8. The molecular weight of PVP K 30 is about 40000 g/mol.

Other particularly well-suited polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115, which are available from BASF.

The use of film-forming hydrophilic polymers from the group of copolymers of polyvinylpyrrolidone has also led to particularly good and washfast color results.

In this context, vinylpyrrolidone-vinyl ester copolymers, such as those sold under the trademark Luviskol® (BASF), can be mentioned as particularly suitable film-forming, hydrophilic polymers. Luviskol® VA 64 and Luviskol® VA 73, each vinylpyrrolidone/vinyl acetate copolymers, are particularly preferred nonionic polymers.

Of the vinylpyrrolidone-comprising copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are very preferably used in the cosmetic compositions.

Vinylpyrrolidone-vinyl acetate copolymers are marketed by BASF SE under the name Luviskol® VA. For example, a VP/vinyl caprolactam/DMAPA acrylates copolymer is sold under the trade name Aquaflex® SF-40 by Ashland Inc. For example, a VP/DMAPA acrylates copolymer is marketed as Styleze CC-10 by Ashland and is a highly preferred vinylpyrrolidone-comprising copolymer.

Other suitable copolymers of polyvinylpyrrolidone may include those obtained by reacting N-vinylpyrrolidone with at least one further monomer selected from the group of V-vinylformamide, vinyl acetate, ethylene, propylene, acrylamide, vinylcaprolactam, vinylcaprolactone and/or vinyl alcohol.

In another very particularly preferred embodiment, a composition (B) is wherein it comprises at least one film-forming hydrophilic polymer selected from the group of polyvinylpyrrolidone (PVP), vinylpyrrolidone/vinyl acetate copolymers, Vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another useful copolymer of vinylpyrrolidone is the polymer known under the INCI name maltodextrin/VP copolymer.

Furthermore, intensively colored keratin material, especially hair, could be obtained with very good wash fastness properties when a nonionic film-forming hydrophilic polymer was used as the film-forming hydrophilic polymer.

In a still further embodiment, it may be preferred if the composition (B) comprises at least one nonionic, film-forming, hydrophilic polymer.

As contemplated herein, a non-ionic polymer is a polymer which, in a protic solvent—such as water, for example—does not carry structural units with permanent cationic or anionic groups under standard conditions, which must be compensated by counterions while maintaining electroneutrality. Cationic groups include, for example, quaternized ammonium groups but not protonated amines. Anionic groups include, for example, carboxylic and sulfonic acid groups.

Compositions (B) which contain, as nonionic, film-forming, hydrophilic polymer, at least one polymer selected from the group of Polyvinylpyrrolidone, copolymers of N-vinylpyrrolidone and vinyl esters of carboxylic acids comprising 2 to 18 carbon atoms, in particular of N-vinylpyrrolidone and vinyl acetate, copolymers of N-vinylpyrrolidone and N-vinylimidazole and methacrylamide, copolymers of N-vinylpyrrolidone and N-vinylimidazole and acrylamide, Copolymers of N-vinylpyrrolidone with N,N-di($C_1$ to $C_4$)alkylamino-($C_2$ to $C_4$)alkyl acrylamide.

If copolymers of N-vinylpyrrolidone and vinyl acetate are used, it is again preferred if the molar ratio of the structural units included from the monomer N-vinylpyrrolidone to the structural units of the polymer included from the monomer vinyl acetate is in the range from 20 to 80 to 80 to 20, in particular from 30 to 70 to 60 to 40. Suitable copolymers of vinylpyrrolidone and vinyl acetate are available, for example, under the trademark Luviskol® VA 37, Luviskol® VA 55, Luviskol® VA 64 and Luviskol® VA 73 from BASF SE.

Another particularly preferred polymer is selected from polymers with the INCI designation VP/Methacrylamide/Vinyl Imidazole Copolymer, which are available, for example, under the trade name Luviset Clear from BASF SE.

Another very particularly preferred nonionic, film-forming, hydrophilic polymer is a copolymer of N-vinylpyrrolidone and N,N-dimethylaminiopropylmethacrylamide, which is sold, for example, by the company ISP under the INCI designation VP/DMAPA Acrylates Copolymer, e.g. under the trade name Styleze® CC 10.

A cationic polymer as contemplated herein is the copolymer of N-vinylpyrrolidone, N-vinylcaprolactam, N-(3-dimethylaminopropyl)methacrylamide and 3-(methacryloylamino)propyl-lauryl-dimethylammonium chloride (INCI name: Polyquaternium-69), which is marketed, for example, under the trade name AquaStyle® 300 (28-32% by weight active substance in ethanol-water mixture, molecular weight 350000) by the company ISP.

Other suitable film-forming hydrophilic polymers include

Vinylpyrrolidone-vinylimidazolium methochloride copolymers as offered under the names Luviquat® FC 370, FC 550 and the INCI name Polyquaternium-16 as well as FC 905 and HM 552, Vinylpyrrolidone-vinylcaprolactam-acrylate terpolymers, such as those offered commercially with acrylic acid esters and acrylic acid amides as the third monomer building block, for example under the name Aquaflex® SF 40.

Polyquaternium-11 is the reaction product of diethyl sulfate with a copolymer of vinylpyrrolidone and dimethylaminoethyl methacrylate. Suitable commercial products are available, for example, under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available, for example, under the name Luviquat® Hold from BASF SE. Polyquaternium-46 is preferably used in an amount of 1 to 5% by weight—based on the total weight of the cosmetic composition. It is particularly preferred that polyquaternium-46 is used in combination with a cationic guar compound. In fact, it is highly preferred that polyquaternium-46 be used in combination with a cationic guar compound and polyquaternium-11.

Suitable anionic film-forming hydrophilic polymers can be, for example, acrylic acid polymers, which can be in uncrosslinked or crosslinked form. Corresponding products are sold commercially under the trade names Carbopol 980, 981, 954, 2984 and 5984 by the company Lubrizol or under the names Synthalen M and Synthalen K by the company 3V Sigma (The Sun Chemicals, Inter Resin).

Examples of suitable film-forming hydrophilic polymers from the group of natural gums are xanthan gum, gellan gum and carob gum.

Examples of suitable film-forming, hydrophilic polymers from the group of polysaccharides are hydroxyethylcellulose, hydroxypropylcellulose, ethylcellulose and carboxymethylcellulose.

Suitable film-forming, hydrophilic polymers from the acrylamide group are, for example, polymers prepared from monomers of (meth)acrylamido-C1-C4-alkyl sulfonic acid or salts thereof. Corresponding polymers may be selected from the polymers of polyacrylamidomethanesulfonic acid, polyacrylamidoethanesulfonic acid, polyacrylamidopropanesulfonic acid, poly-2-acrylamido-2-methylpropanesulfonic acid, poly-2-methylacrylamido-2-methylpropanesulfonic acid, and/or poly-2-methylacrylamido-n-butanesulfonic acid.

Preferred polymers of poly(meth)arylamido-C1-C4-alkyl-sulfonic acids are crosslinked and at least 90% neutralized. These polymers can be crosslinked or non-crosslinked.

Cross-linked and fully or partially neutralized polymers of the poly-2-acrylamido-2-methylpropane sulfonic acid type are available under the INCI names "Ammonium Polyacrylamido-2-methyl-propanesulphonate" or "ammonium polyacryldimethyltauramide".

Another preferred polymer of this type is the crosslinked poly-2-acrylamido-2methyl-propanesulfonic acid polymer sold by Clariant under the trade name Hostacerin AMPS, which is partially neutralized with ammonia.

In another explicitly very particularly preferred embodiment, a process is wherein the composition (B) comprises at least one anionic, film-forming, polymer.

In this context, the best results were obtained when the composition (B), comprises at least one film-forming polymer comprising at least one structural unit of formula (P-I) and at least one structural unit of formula (P-II)

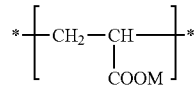
(P-I)

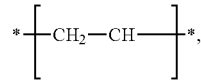
(P-II)

where
M represents a hydrogen atom or ammonium (NH$_4$), sodium, potassium, ½ magnesium or ½ calcium.

When M represents a hydrogen atom, the structural unit of the formula (P-I) is based on an acrylic acid unit.

When M stands for an ammonium counterion, the structural unit of the formula (P-I) is based on the ammonium salt of acrylic acid.

When M represents a sodium counterion, the structural unit of the formula (P-I) is based on the sodium salt of acrylic acid.

When M stands for a potassium counterion, the structural unit of the formula (P-I) is based on the potassium salt of acrylic acid.

If M stands for a half equivalent of a magnesium counterion, the structural unit of the formula (P-I) is based on the magnesium salt of acrylic acid.

If M stands for a half equivalent of a calcium counterion, the structural unit of the formula (P-I) is based on the calcium salt of acrylic acid.

The film-forming polymer or polymers are preferably used in specific ranges of amounts in composition (B). In this context, it has proved particularly preferable for solving the problem as contemplated herein if the composition (B) comprises—in each case based on its total weight—one or more film-forming polymers in a total amount of from 0.1 to 18.0% by weight, preferably from 1.0 to 16.0% by weight, more preferably from 5.0 to 14.5% by weight and very particularly preferably from 8.0 to 12.0% by weight.

In a further preferred embodiment, a process is wherein the composition (B) comprises—based on its respective total weight—one or more film-forming polymers in a total amount of from 0.1 to 18.0% by weight, preferably from 1.0 to 16.0% by weight, more preferably from 5.0 to 14.5% by weight and most preferably from 8.0 to 12.0% by weight.

Coloring Compounds in the Composition (B)

In the case that the composition (B) further comprises one or more film-forming polymers, it may be preferred that the composition (B) also further comprises at least one colorant compound selected from the group of pigments and direct dyes.

The coloring compounds which may be used in composition (B) are any coloring compounds from the group comprising pigments and direct dyes which are known to be suitable for use in composition (A).

Other Cosmetic Ingredients in the Composition (B)

In addition, the composition (B) may also contain one or more further cosmetic ingredients.

The cosmetic ingredients that may be optionally used in the composition (B) may be any suitable ingredients to impart further beneficial properties to the composition. For example, in the composition (A), a solvent, a thickening or film-forming polymer, a surface-active compound from the group of nonionic, cationic, anionic or zwitterionic/amphoteric surfactants, oxidation dye precursors, the fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

The selection of these further substances will be made by the skilled person according to the desired properties of the compositions. With regard to further optional components as well as the quantities of these components used, reference is expressly made to the relevant manuals known to the skilled person.

Application of the Compositions (A) and (B)

The method involves the application of both compositions (A) and (B) to the keratinous material. The two compositions (A) and (B) are two different compositions.

As described previously, it is particularly preferred if the composition (A) is first applied to the keratin material, and subsequently the composition (B) is applied to the keratin material in the form of an aftertreatment agent.

In the context of a further embodiment, a method comprising the following steps is particularly preferred:
(1) Application of the first composition (A) to the keratin material,
(2) Allowing the composition (A) to act on the keratin material for a period of about 1 to about 10 minutes, preferably about 1 to about 5 minutes,
(3) Rinsing the composition (A) out of the keratin material,
(4) Application of composition (B) to the keratin material,
(5) Allowing the composition (B) to act on the keratin material for a period of about 1 to about 10 minutes, preferably about 1 to about 5 minutes,
(6) Rinsing the composition (B) out of the keratin material.

By rinsing the keratinous material with water in steps (3) and (6) of the process, it is understood as contemplated herein that only water is used for the rinsing process, without the use of other compositions different from compositions (A) and (B).

In a step (1), the composition (A) is first applied to the keratin materials, especially human hair.

After application, the composition (A) is allowed to act on the keratin materials. In this context, exposure times of about 10 seconds to about 10 minutes, preferably about 20 seconds to about 5 minutes and most preferably about 30 seconds to about 2 minutes on the hair have proven to be particularly advantageous.

In a preferred embodiment of the method, the composition (A) can now be rinsed from the keratin materials before the composition (B) is applied to the hair in the subsequent step.

In step (4), the composition (B) is now applied to the keratin materials. After application, the composition (B) is now left to act on the hair.

The process allows the production of dyeings with particularly good intensity, friction resistance and wash fastness even with a short exposure time of the compositions (A) and (B). Exposure times of about 10 seconds to about 10 minutes, preferably about 20 seconds to about 5 minutes and most preferably about 30 seconds to about 3 minutes on the hair have proven to be particularly advantageous.

In step (6), the composition (B) is now rinsed out of the keratin material with water.

In the context of a further embodiment, a method comprising the following steps in the order indicated is particularly preferred:
(1) Application of the first composition (A) to the keratin material,
(2) Allowing the composition (A) to act on the keratin material for a period of about 1 to about 10 minutes, preferably about 1 to about 5 minutes,
(3) Rinsing the composition (A) out of the keratin material,
(4) Application of composition (B) to the keratin material,
(5) Allowing the composition (B) to act on the keratin material for a period of about 1 to about 10 minutes, preferably about 1 to about 5 minutes,
(6) Rinsing the composition (B) out of the keratin material.

the compositions required, in particular for the dyeing process, are provided in the form of a multi-component packaging unit (kit-of-parts).

A second object of the present disclosure is a multi-component packaging unit (kit-of-parts) for dyeing keratinous material, comprising separately prepared
a first container comprising a first composition (A), and
a second container comprising a second composition (B), wherein
wherein the compositions (A) and (B) have already been disclosed in detail in the description of the first subject matter of the present disclosure.

Furthermore, the multi-component packaging unit may also comprise further packaging units, each comprising a cosmetic composition. These compositions may contain ingredients that are chemically and/or physically incompatible with ingredients of composition (A) and/or (B).

In particular, composition (A) comprises, with the alkoxysilanes, a class of highly reactive compounds that can undergo hydrolysis or oligomerization and/or polymerization during their application.

To avoid premature oligomerization or polymerization, it may be of significant advantage to the user to prepare the ready-to-use composition (A) just prior to application.

In a preferred embodiment, therefore, a multicomponent packaging unit (kit-of-parts) for dyeing keratinous material, separately prepared, comprises
a first container having a first composition (A') comprising one or more $C_1$-$C_6$ organic alkoxysilane sand/or condensation products thereof,
a second container with a second composition (A") comprising at least one colorant compound selected from the group of pigments and direct dyes, and
a third container having a third composition (B) comprising tannic acid,
wherein the essential ingredients of the compositions (A'), (A") and (B) of the present disclosure have already been disclosed in detail in the description of the first subject matter of the present disclosure.

In another preferred embodiment, a multicomponent packaging unit (kit-of-parts) for dyeing keratinous material, separately prepared, comprises
a first container having a first composition (A') comprising one or more $C_1$-$C_6$ organic alkoxysilanes and/or condensation products thereof,
a second container with a second composition (A") comprising at least one colorant compound selected from the group of pigments and direct dyes,
a third container having a third composition (A") comprising water, and
a fourth container having a fourth composition (B) comprising tannic acid,
wherein the essential ingredients of the compositions (A'), (A"), (A") and (B) of the present disclosure have already been disclosed in detail in the description of the first subject matter of the present disclosure.

With regard to the other preferred embodiments of the multicomponent packaging units, the same applies mutatis mutandis as to the process.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method of dyeing keratinous material, the method comprising the steps of:
applying a first composition (A) to the keratinous material, the first composition (A) comprising:
(A1) one or more organic $C_1$-$C_6$ alkoxysilanes and/or condensation products thereof, and
(A2) at least one colorant compound selected from the group of pigments, direct dyes, or combinations thereof, and
applying a second composition (B) to the keratinous material, the second composition (B) comprising:
(B1) Tannic acid.

2. The process according to claim 1, wherein the first composition (A) comprises one or more organic $C_1$-$C_6$ alkoxysilanes (A1) of the formula (S-I) and/or (S-II), $$R_1R_2N\text{-}L\text{-}Si(OR_3)_a(R_4)_b \quad \text{(S-I)}$$

where
$R_1,R_2$ independently represent a hydrogen atom or a $C_1$-$C_6$ alkyl group,
L is a linear or branched, divalent $C_1$-$C_{20}$ alkylene group,
$R_3,R_4$ are independent of each other for a $C_1$-$C_6$ alkyl group,
a, represents an integer from 1 to 3, and
b is the integer 3-a, and $$(R_5O)_c(R_6)_d Si\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad \text{(S-II)},$$

where
$R_5$, $R_{5'}$, $R_{5''}$, $R_6$, $R_{6'}$ and $R_{6''}$ independently represent a $C_1$-$C_6$ alkyl group,
A, A', A'', A''' and A'''' independently represent a linear or branched $C_1$-$C_{20}$ divalent alkylene group,
$R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (S-III), $$(A'''')\text{-}Si(R_6'')_{d''}(OR_5'')_{c''} \quad \text{(S-III)}$$

c, stands for an integer from 1 to 3,
d stands for the integer 3-c,
c' stands for an integer from 1 to 3,
d' stands for the integer 3-c',
c'' stands for an integer from 1 to 3,
d'' stands for the integer 3-c'',
e stands for 0 or 1,
f stands for 0 or 1,
g stands for 0 or 1,
h stands for 0 or 1,
wherein at least one of the radicals from e, f, g and h is different from 0,
and/or condensation products thereof.

3. The process according claim 1, wherein the first composition (A) comprises at least one $C_1$-$C_6$ organic alkoxysilane (A1) selected from the group of
(3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-dimethylaminoethyl)triethoxysilane,
(2-Dimethylaminoethyl)trimethoxysilane
and/or condensation products thereof, or combinations thereof.

4. The process according to claim 1, wherein the first composition (A) comprises one or more organic $C_1$-$C_6$ alkoxysilanes (A1) of the formula (S-IV), $$R_9Si(OR_{10})_k(R_{11})_m \quad \text{(S-IV)},$$

where
$R_9$ represents a $C_1$-$C_{12}$ alkyl group,
$R_{10}$ stands for a $C_1$-$C_6$ alkyl group,
$R_{11}$ stands for a $C_1$-$C_6$ alkyl group
k is an integer from 1 to 3, and
m stands for the integer 3-k,
and/or condensation products thereof.

5. The process according to claim 1, wherein the first composition (A) comprises at least one $C_1$-$C_6$ organic alkoxysilane (A1) selected from the group of
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane,
Octadecyltrimethoxysilane,
Octadecyltriethoxysilane,
their mixtures
and/or condensation products thereof, or combinations thereof.

6. The process according to claim 1, wherein the first composition (A) comprises at least one inorganic pigment (A2) selected from the group of colored metal oxides, metal hydroxides, metal oxide hydrates, silicates, metal sulfides, complex metal cyanides, metal sulfates, bronze pigments, colored mica- or mica-based pigments coated with at least one metal oxide and/or metal oxychloride, or combinations thereof.

7. The process according to claim 1, characterized in that the first composition (A) comprise at least one pigment (A2) chosen from the group of pigments based on a lamellar substrate platelet, pigments based on a lenticular substrate platelet, pigments based on a substrate platelet comprising a vacuum-metallized pigment, pigments based on a substrate platelet comprising synthetic mica, or combinations thereof.

8. The process according to claim 1, wherein the second composition (B) further comprises at least one pigment selected from the group of pigments based on a lamellar substrate platelet, pigments based on a lenticular substrate platelet, pigments based on a substrate platelet comprising a vacuum metallized pigment, pigments based on a substrate platelet comprising artificial mica, or combinations thereof.

9. The process according to claim 1, wherein the second composition (B) further comprises at least one film-forming polymer.

10. The process according to claim 1, wherein the second composition (B) further comprises an antioxidant.

11. The process according to claim 1, wherein the first composition (A) comprises:
- at least one first pigment (A2) selected from the group of colored metal oxides, metal hydroxides, metal oxide hydrates, silicates, metal sulfides, complex metal cyanides, metal sulfates, bronze pigments, mica- or mica-based colored pigments coated with at least one metal oxide and/or metal oxychloride, or combinations thereof; and
- at least one second pigment (A2) selected from the group of pigments based on a lamellar substrate platelet, pigments based on a lenticular substrate platelet, pigments based on a substrate platelet comprising a vacuum metallized pigment, pigments based on a substrate platelet comprising artificial mica, or combinations thereof.

12. A multi-component packaging unit (kit-of-parts) for dyeing keratinous material, comprising separately prepared
- a first container having a first composition (A) comprising
  - (A1) one or more $C_1$-$C_6$ organic alkoxysilanes and/or condensation products thereof, and
  - (A2) at least one colorant compound selected from the group of pigments and direct dyes, and
- a second container having a second composition (B) comprising (B1) tannic acid.

13. A multi-component packaging unit (kit-of-parts) for dyeing keratinous material, separately assembled
- a first container having a first composition (A') comprising one or more $C_1$-$C_6$ organic alkoxysilanes and/or condensation products thereof,
- a second container with a second composition (A") comprising at least one colorant compound selected from the group of pigments and direct dyes, and
- a third container having a third composition (B) comprising tannic acid.

14. The multi-component packaging unit (kit-of-parts) according to claim 13 further comprising;
- a fourth container having a fourth composition comprising water.

* * * * *

UNITED STATES PATENT AND TRADEMARK OFFICE
CERTIFICATE OF CORRECTION

PATENT NO. : 11,896,701 B2
APPLICATION NO. : 17/785874
DATED : February 13, 2024
INVENTOR(S) : Phillip Jaiser et al.

Page 1 of 1

It is certified that error appears in the above-identified patent and that said Letters Patent is hereby corrected as shown below:

In the Specification

Column 7, Line 59 change "-[NR-(A")]$_h$" to -- -[NR$_8$-(A")]$_h$--.

Column 17, Line 18 change "+EtOH" to --+MeOH--.

Column 27, Line 54 change "3-methacryloxy-propyltriethoxysilane" to --3-methacryloxypropyltriethoxysilane--.

Column 27, Line 58-59 change "3-methacryloxy-propyltris(propoxy)silane" to --3-methacryloxypropyltris(propoxy)silane--.

Column 27, Line 60 change "3-acryloxy-propyltris(methoxyethoxy)silane" to --3-acryloxypropyltris(methoxyethoxy)silane--.

Column 40, Line 3 change " 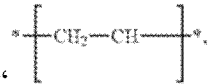 " to -- 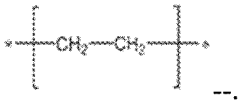 --.

Signed and Sealed this
Fourth Day of June, 2024

Katherine Kelly Vidal
*Director of the United States Patent and Trademark Office*